(12) United States Patent
Rakic et al.

(10) Patent No.: US 9,999,595 B2
(45) Date of Patent: Jun. 19, 2018

(54) EYE DEVICE

(71) Applicant: EYED PHARMA, Liège (BE)

(72) Inventors: Jean-Marie Rakic, Havelange (BE); Jean-Michel Foidart, Trooz (BE)

(73) Assignee: EYED PHARMA, Liège (BE)

( * ) Notice: Subject to any disclaimer, the term of this patent is extended or adjusted under 35 U.S.C. 154(b) by 13 days.

(21) Appl. No.: 15/034,869

(22) PCT Filed: Nov. 14, 2014

(86) PCT No.: PCT/EP2014/074644
§ 371 (c)(1),
(2) Date: May 5, 2016

(87) PCT Pub. No.: WO2015/071427
PCT Pub. Date: May 21, 2015

(65) Prior Publication Data
US 2016/0287513 A1 Oct. 6, 2016

(30) Foreign Application Priority Data

Nov. 14, 2013 (EP) ..................................... 13192889

(51) Int. Cl.
A61K 9/00 (2006.01)
A61K 47/34 (2017.01)
A61K 47/32 (2006.01)
A61K 31/5377 (2006.01)
A61F 9/00 (2006.01)

(52) U.S. Cl.
CPC .......... *A61K 9/0051* (2013.01); *A61F 9/0017* (2013.01); *A61K 31/5377* (2013.01); *A61K 47/32* (2013.01); *A61K 47/34* (2013.01); *A61F 2240/005* (2013.01)

(58) Field of Classification Search
None
See application file for complete search history.

(56) References Cited

U.S. PATENT DOCUMENTS

| 3,710,795 A | 1/1973 | Higuchi et al. |
| 4,069,307 A | 1/1978 | Higuchi et al. |
| 4,718,905 A * | 1/1988 | Freeman ................. A61L 27/30 427/2.24 |
| 4,959,217 A | 9/1990 | Sanders et al. |

(Continued)

OTHER PUBLICATIONS

Search Report with Written Opinion corresponding to European Patent Application No. 13192889.7, dated Jul. 31, 2014.

(Continued)

*Primary Examiner* — Carlos A Azpuru
*Assistant Examiner* — Casey S Hagopian
(74) *Attorney, Agent, or Firm* — Lathrop Gage LLP; James H. Velema, Esq.

(57) ABSTRACT

The invention provides a sustained release intraocular drug delivery device comprising: (a) a polymeric matrix core into which at least one therapeutic agent is mixed, and; (b) a polymeric coating completely surrounding said polymeric matrix material; wherein said polymeric matrix core and polymeric coating are insoluble and inert in ocular fluids, and wherein said sustained release intraocular drug delivery device has a compliant annular segment shape and is to be inserted into the sulcus of the intact and/or pseudophakic eye.

30 Claims, 13 Drawing Sheets

(56) References Cited

U.S. PATENT DOCUMENTS

| | | | | |
|---|---|---|---|---|
| 5,928,282 | A | * | 7/1999 | Nigam ................. A61F 2/16 623/6.43 |
| 6,494,910 | B1 | | 12/2002 | Ganem et al. |
| 2006/0074487 | A1 | | 4/2006 | Gilg |
| 2009/0018650 | A1 | | 1/2009 | Boxer Wachler |
| 2010/0226962 | A1 | | 9/2010 | Rodstrom et al. |
| 2013/0017243 | A1 | * | 1/2013 | Shi ................. A61K 9/0051 424/427 |

OTHER PUBLICATIONS

International Search Report with Written Opinion corresponding to International Patent Application No. PCT/EP2014/074644, dated Jan. 23, 2015.

\* cited by examiner

A

B

EYE DEVICE

RELATED APPLICATIONS

This application is a 35 U.S.C. § 371 filing of International Application No. PCT/EP2014/074644, filed Nov. 14, 2014, which claims priority to European Patent Application No. 13192889.7, filed Nov. 14, 2013. The entire contents of each are incorporated herein by reference.

TECHNICAL FIELD OF THE INVENTION

The present invention relates to a sustained release intraocular drug delivery device, more particularly, a removable sustained release intraocular drug delivery device intended for the prolonged and controlled release of one or more therapeutic agent.

BACKGROUND OF THE INVENTION

The treatment of many diseases and disorders of the eye, especially in case of degenerative or persistent conditions, poses challenges of achieving and maintaining adequate therapeutic drug concentrations within the eye and its surrounding structures. For instance, oral therapies for the eye often only result in negligible actual absorption of the drug in the ocular tissues due to low bioavailability of the drug. Ocular drug levels following systemic administration of drugs, are usually limited by the blood/ocular barriers (i.e. tight junctions between the endothelial cells of the capillaries), limiting entry of drugs into the eye. In addition, serious adverse side effects have been associated with systemic administration of certain drugs for use in treating eye-related disorders. For example, systemic treatments of the eye using the immune response modifier cyclosporine A, have the potential to cause nephrotoxicity or increase the risk of opportunistic infections.

The most common method of drug administration to the eyes is therefore by topical administration, which is mostly achieved by way of ophthalmic drops and/or topical ointments containing the medicament. This type of drug delivery however has only limited and often variable penetration to the anterior chamber of the eye. In addition, adequate therapeutic levels of the drug are rarely achieved and sustained in e.g. the middle or back portions of the eye. This is a major drawback, as the posterior chamber of the eye is a frequent site of inflammation or the site of action where ocular drug therapy should is targeted to for many indications. Topical administration in the form of drops and ointments also poses the difficulty of adjusting the dose, as patients often administer too much or too little of the composition. It is also the most difficult treatment option in which to achieve patient compliance, since patients tend to forget to apply the compositions, particularly in the treatment of degenerative or persistent conditions.

As an approach for circumventing the drawbacks encountered by local topical delivery, local therapy routes for the eye involving direct intravitreal injection of a drug through the sclera (i.e. the spherical, collagen-rich outer covering of the eye) have been tried.

However, the intravitreal injection delivery route tends to result in a short half life and rapid clearance of the drug, without sustained release capability being attained. Consequently, monthly injections are frequently required to maintain therapeutic ocular drug levels which is not practical for many patients, particularly in the treatment of degenerative or persistent conditions. Moreover, monthly intravitreal injections are not without risk, as some undesired effects associated with repeated injections can occur including sub-conjunctival hemorrhage, intraocular infections, worsening of pre-existing cataracts, accidental lesion to the lens, and/or retinal detachment.

Implantable intraocular sustained-release delivery devices have the potential to avoid the shortcomings and complications that can arise from both systemic and local therapies (i.e. topical administration or intravitreal injections). However, despite the variety of ocular implant devices which have been described and used in the art, the full potential of this therapy route has not been reached.

A common approach is the use of biodegradable implants (See U.S. Pat. Nos. 5,164,188, 5,824,072, 5,476,511, 4,997,652, 4,959,217, 4,668,506, and 4,144,317); however, such implants do not allow prolonged residence time with a guarantee of suitable release of the active substance (i.e. the release of the drug may change throughout the residence period). Other devices, such as the ones described in U.S. Pat. No. 4,014,335, 3,416,530 or 3,618,604, comprise multiple layers and are complicated in their design and manufacture, increasing the likelihood of product variability or the need to comprise additional osmotic or ionic agents which may not be compatible with the ocular environment.

Also, accidental movement of the insert in the eye is frequently observed, the insert passing either behind the eye or leaving the socket.

In view of the above, there remains a need in the art for improved sustained release intraocular drug delivery devices, which are simple to manufacture, and capable of releasing a therapeutic agent at a sustained and controlled rate for extended periods of time, while reducing the likelihood of implant rejection.

US 2006/0074487 describes a device configured for the sulcus of the eye. The device is used for treating an ocular condition linked to a diminution of the amplitude of the eye due to a loss of tension of the zonular fibres caused by an increase of the diameter of the lens. The device comprises a closed tubular envelope made of an elastic and fluid-impermeable material. The inner ring wall of the envelope delimits a lumen adapted to be filled with an incompressible fluid. The envelope can be impregnated by a composition containing an active ingredient or a combination of active ingredients of a medicine. This device does however not guarantee sustained and controlled release of the medicine(s).

SUMMARY OF THE INVENTION

Accordingly, it is the object of the present application to provide an improved sustained release intraocular drug delivery device, which solves at least some of the problems mentioned above.

The present inventors have designed an insoluble and inert sustained release intraocular drug delivery device, for insertion in the sulcus of the eye. The insertion of the device in the sulcus of the eye does not initiate fibrotic processes and due to its inert nature in ocular fluids, the device can be removed after it has been depleted from its drug or earlier, in case of unwanted side-effect to the drug. Moreover, using the sulcus of the eye as insertion site allows the dimensions of the device to be such that sustained release of the therapeutic agent of choice can be attained for up to two years. In addition, the inventors have discerned a simple method of manufacture of said intraocular device, allowing attaining product uniformity by standard manufacturing techniques.

According to a first aspect of the present application, a sustained release intraocular drug delivery device is provided comprising:
(a) a polymeric matrix core into which at least one therapeutic agent is mixed, and;
(b) a polymeric coating completely surrounding said polymeric matrix material;

wherein said polymeric matrix core and polymeric coating are insoluble and inert in ocular fluids, and wherein said sustained release intraocular drug delivery device has an annular shape. Preferably, said device comprises an annual compliant segment, wherein said segment can range from 90 to 360°. More preferably, said device is configured for insertion into the sulcus of the eye, even more preferably, said device has a cross sectional diameter ranging from 0.10 to 0.80 mm, According to a preferred embodiment, said sustained release intraocular drug delivery device contains a therapeutic agent for treating an eye-related disorder, which may be selected from the group consisting of antibiotic agents, antibacterial agents, antiviral agents, prostaglandin analogues, anti-glaucoma agents, antiallergenic agents, anti-inflammatory agents, anti-angiogenesis agents, immune system modifying agents, anti-cancer agents, antisense agents, antifungal agents, myotic and anticholinesterase agents, mydriatic agents, differentiation modulator agents, sympathomimetic agents, anaesthetic agents, vasoconstrictive agents, vasodillatory agents, decongestants, cell transport/mobility impending agents, polypeptides and protein agents, steroidal agents, carbonic anhydrase inhibitor agents, polycations, polyanions, and lubricating agents.

In a preferred embodiment, said sustained release intraocular drug delivery device contains a therapeutic agent which may be selected from the group consisting of bevacizumab, ranibizumab, aflibercept, timolol, latanoprost, dorzolamide, triamcinolone, dexamethasone or cyclosporin.

In a second aspect of the present application relates to a therapeutic agent for use in the treatment of ocular diseases, wherein said therapeutic agent is administered in a sustained release intraocular drug delivery device according to the first aspect of the present application, and wherein said sustained release intraocular drug delivery device is inserted into the sulcus of the eye. In a preferred embodiment, said therapeutic agent for use is selected from the group comprising antibiotic agents, antibacterial agents, antiviral agents, prostaglandin analogues, anti-glaucoma agents, antiallergenic agents, anti-inflammatory agents, anti-angiogenesis agents, immune system modifying agents, anti-cancer agents, antisense agents, antifungal agents, myotic and anticholinesterase agents, mydriatic agents, differentiation modulator agents, sympathomimetic agents, anaesthetic agents, vasoconstrictive agents, vasodillatory agents, decongestants, cell transport/mobility impending agents, polypeptides and protein agents, steroidal agents, carbonic anhydrase inhibitor agents, polycations, polyanions, and lubricating agents.

More preferably, said therapeutic agent for use is selected from the group consisting of bevacizumab, ranibizumab, aflibercept, timolol, latanoprost dorzolamide, triamcinolone, dexamethasone or cyclosporine.

A third aspect of the present application deals with a method of treating ocular diseases comprising administering a therapeutically effective amount of a therapeutic agent for treating eye-related disorders, wherein said agent is administered in a sustained release intraocular drug delivery device according to the first aspect of the present application, and wherein said sustained release intraocular drug delivery device is inserted into the sulcus of the eye, such that the ocular disease is treated. Preferably, said agent is selected from the group consisting of bevacizumab, ranibizumab, aflibercept, timolol, latanoprost dorzolamide, triamcinolone, dexamethasone or cyclosporine. The invention further provides for a surgical method comprising the step of inserting the intraocular drug delivery device according to the invention into the sulcus of the eye.

A fourth aspect of the present application provides a process for preparing a sustained release intraocular drug delivery device according to the first aspect of the present application, comprising:
mixing the at least one therapeutic agent with an insoluble and inert polymer;
molding and/or extruding said mixture to afford a polymeric matrix core; and,
providing the resulting polymeric matrix core with a polymeric coating.

The invention hence provides for a method of manufacturing an intraocular drug delivery device according to the invention for use in treating eye-related disorders.

DETAILED DESCRIPTION OF THE INVENTION

Figure 1:
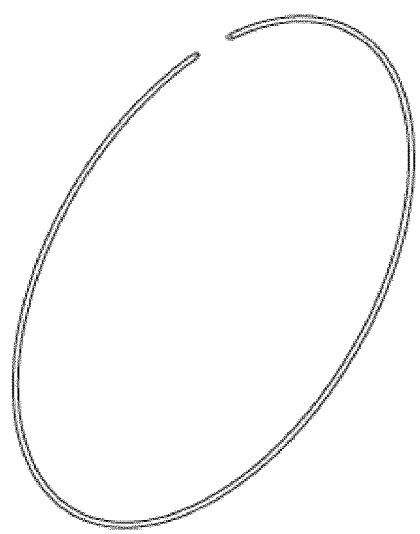
FIG. 1A, shows a three-dimensional representation of the polymeric matrix of the intraocular drug delivery device, according to an embodiment of the present application.
FIG. 1B, shows a side view of the polymeric matrix of the intraocular drug delivery device, according to an embodiment of the present application.
Figure 1:
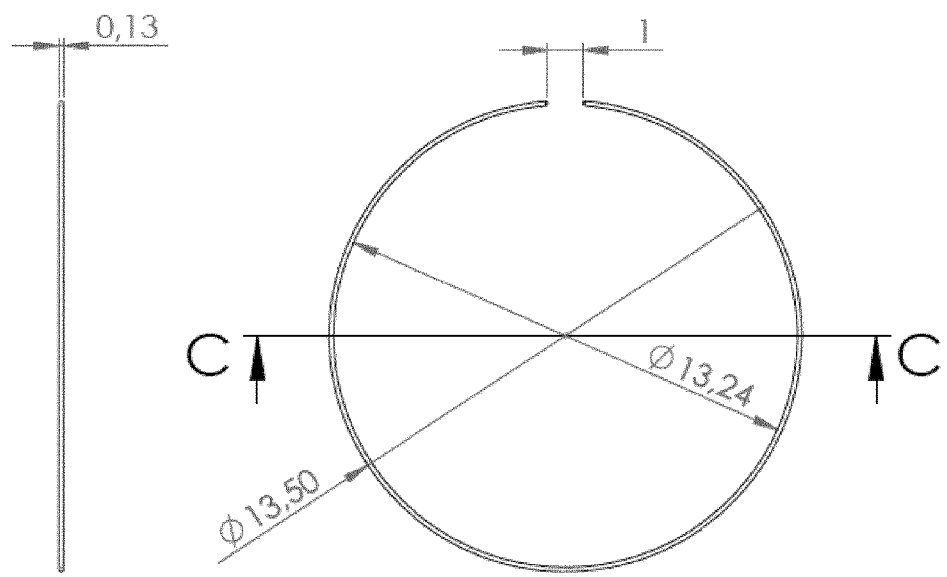

Before the present methods used in the application are described, it is to be understood that this application is not limited to particular methods, components, or devices described, as such methods, components, and devices may, of course, vary. It is also to be understood that the terminology used herein is not intended to be limiting, since the scope of the present application will be limited only by the appended claims.

Unless defined otherwise, all technical and scientific terms used herein have the same meaning as commonly understood by one of ordinary skill in the art to which this application belongs. Although any methods and materials similar or equivalent to those described herein may be used in the practice or testing of the present application, the preferred methods and materials are now described.

As used herein, the singular forms "a", "an", and "the" include both singular and plural referents unless the context clearly dictates otherwise. The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints. When a numerical value is used, said value encompasses the exact numerical value as such, as well as all numerical values that would be rounded up to said exact numerical value according to standard mathematical and/or statistical regulations. For example, a ring's annular segment of "180 degrees" encompasses the angle values of 179 and 181 degrees, more in particular 179.5; 179.6; 179.7; 179.8; 179.9; 180.0; 180.1; 180.2; 180.3; and 180.4 degrees. When this is used in combination with the term "about", said ring's annular segment also encompasses angles that differ from said exact angle by 0.1, 0.2, 0.3, 0.4, 0.5, 0.6, 0.7, 0.7, 0.9, or 1.0 degree. The skilled person will appreciate that when the dimensions of the sustained release intraocular drug delivery device are expressed in length units, the same principle applies; for example a length of "14.0 mm" encompasses length values of 13 to 15 mm, more in particular of 13.5; 13.6; 13.7; 13.8; 13.9; 14.0; 14.1; 14.2; 14.3; and 14.4 mm. Thus, the term "about 14.0 mm" encompasses lengths that differ from said exact length by 0.1, 0.2, 0.3, 0.4, 0.5, 0.6, 0.7, 0.7, 0.9, or 1.0 mm.

Similarly, when a period of time is indicated using a numerical value such as "about 30 minutes", said value encompasses the exact time indicated as well as periods that deviate therefrom by e.g. less than one minute, half a minute, or 1, 2, 3, 4 or 5 minutes. Analogously, the term "about 30 seconds" encompasses about 20, 25 seconds to about 35, 40 seconds, as well as any time in between.

As used throughout the present disclosure, the terms "concentration" and "content" are used interchangeably and refer to the weight concentration or mass fraction of a constituent, i.e. the mass of a constituent divided by the total mass of all constituents, and is expressed in % by weight or % w/w.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed. All documents cited in the present specification are hereby incorporated by reference in their entirety.

Reference throughout this specification to "one embodiment" or "an embodiment" means that a particular feature, structure or characteristic described in connection with the embodiment is included in at least one embodiment of the present application. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the application, and form different embodiments, as would be understood by those in the art. For example, in the claims, any of the claimed embodiments can be used in any combination.

By means of further guidance, definitions for the terms used in the description are included to better appreciate the teachings of the present application.

One aspect of the present application provides a sustained release intraocular drug delivery device comprising:
 (a) a matrix core containing at least one therapeutic agent, and;
 (b) a polymeric coating completely surrounding said matrix core;
wherein said matrix core and polymeric coating are insoluble and inert in ocular fluids, and wherein said sustained release intraocular drug delivery device is configured for the sulcus of the eye.

Preferably, said device comprises or is formed of a compliant annular segment configured for the sulcus of the eye. More specifically, said device has a cross sectional diameter ranging from 0.10 to 0.80 mm. The annular segment can be ranging from 90 to 360° of the ring. Preferably, said annular segment ranges from 180 to 360°, more preferably from 300 to 360° of the ring. The annular segment may have an external or outer diameter ranging from 5.0 to 15.0 mm, preferably from 10.0 to 15.0 mm, more preferably from 13.0 to 14.0 mm, such as about 13.5 mm. With the "external diameter" or "outer diameter" of an annulus or an annular segment is meant herein the diameter of the outer circle of the annulus or the annulus segment.

A "sustained release" dosage form is designed to release a drug at a predetermined rate in order to maintain a constant drug concentration for a specific period of time.

As used herein, the term "therapeutic agent" or "compound" is used interchangeably with "drug", and refers to a chemical substance used in the treatment, cure, prevention, or diagnosis of a disease.

As used herein, an "intraocular drug delivery device" refers to an apparatus that is structured, sized, or otherwise configured to be placed in an eye; and once placed, locally release a drug of choice. Intraocular drug delivery devices of the present application may be biocompatible with physiological conditions of an eye and do not cause adverse side effects in normal eyes and/or in pseudophakic eyes. Intraocular drug delivery devices according to the present application may be placed in an eye without disrupting vision of the eye.

As used herein, a "pseudophakic eye" refers to an eye in which an intraocular lens has been implanted. The intraocular lens may replace a crystalline lens that is damaged, due to for example a perforating wound or ulcer; or does not function properly, for example in the case of cataracts or myopia. The intraocular lens may be also implanted in patients whose crystalline lens is absent due to congenital anomaly.

The "matrix core" of the sustained release intraocular drug delivery device of the present application is located in the innermost part of the present device. It comprises a material, which is insoluble and inert in ocular fluids (i.e. biocompatible) while at the same time it is not absorbed or degraded by the eye tissues. The use of rapidly dissolving materials or materials highly soluble in eye fluids is to be avoided since dissolution of the wall would affect the constancy of the drug release, as well as the capability of the device to remain in place for a prolonged period of time. Preferred materials used for the matrix core of the sustained release intraocular drug delivery device of the present application include, for example polymers or stent material, such as nitinol.

Nitinol is a metal alloy of nickel and titanium, where the two elements are present in roughly equal atomic percentages. Nitinol alloys exhibit two particular properties: shape memory and superelasticity. The term "shape memory" refers to the ability of the alloy to undergo deformation at one temperature, and then recover its original shape upon heating. The term "superelasticity" refers to the ability of the alloy to exhibit enormous elasticity, some 10 to 30 times that of ordinary metal. Nitinol alloys are both corrosion resistant and biocompatible.

The matrix core of the sustained release intraocular drug delivery device of the present invention also comprises at least one therapeutic agent. The matrix core of the sustained release intraocular drug delivery device of the present invention may comprise from 0.1 to 50% by weight of the at least one therapeutic agent based on the total weight of polymeric matrix material. Preferably, the matrix core comprises from 1.0 to 50% by weight of said at least one therapeutic agent based on the total weight of polymeric matrix material.

The matrix core of the sustained release intraocular drug delivery device of the present invention is characterized in that the therapeutic agent is dispersed or distributed therethrough, i.e. the at least one therapeutic agent is mixed into the matrix core, preferably the polymeric matrix core. Dispersion of the therapeutic agent into the matrix core can be achieved by e.g. cross-linking a blend of a crosslinkable polymer (e.g. PDMS) and the at least one therapeutic agent, or by co-extrusion of a thermoplastic polymer (e.g. EVA, PE, preferably HDPE, PMMA) and the at least one therapeutic agent.

In an embodiment, the matrix core of the sustained release intraocular drug delivery device of the present application is made of nitinol stent material.

In another embodiment, the matrix core of the sustained release intraocular drug delivery device of the present application is made of a polymer.

According to a first aspect of the present application, a sustained release intraocular drug delivery device is provided comprising:
(a) a polymeric matrix core into which at least one therapeutic agent is mixed, and;
(b) a polymeric coating completely surrounding said polymeric matrix material;
wherein said polymeric matrix core and polymeric coating are insoluble and inert in ocular fluids, and wherein said sustained release intraocular drug delivery device is configured for the sulcus of the eye.

Preferably, said device comprises or is formed of a compliant annular segment configured for the sulcus of the eye. More specifically, said device has a cross sectional diameter ranging from 0.10 to 0.80 mm. The annular segment can be ranging from 90 to 360° of the ring. Preferably, said annular segment ranges from 180 to 360°, more preferably from 300 to 360° of the ring.

The "polymeric matrix core" of the sustained release intraocular drug delivery device of the present application is located in the innermost part of the present device. It comprises a polymer, which is insoluble and inert in ocular fluids (i.e. biocompatible) while at the same time it is not absorbed or degraded by the eye tissues. The use of rapidly dissolving materials or materials highly soluble in eye fluids is to be avoided since dissolution of the wall would affect the constancy of the drug release, as well as the capability of the device to remain in place for a prolonged period of time.

As used herein, the term "polymer" refers to a molecule whose structure is composed of multiple repeating units. A "biocompatible polymer" is thus a polymer that is tolerated by living organisms. It may be of natural or synthetic origin.

Various polymers can be used to form the polymeric matrix core having the therapeutic agent distributed therethrough. Preferably, the polymer is chemically compatible with the therapeutic agent and permeable to the therapeutic agent.

Polymers suitable for the polymeric matrix core include, for example: ethylene-co-vinylacetate (EVA), poly(dimethylsiloxane) (PDMS), polypropylene (PP), polyethylene (PE), preferably high density polyethylene (HDPE), (plasticized) polyethylene terephthalate (PET), poly(methyl methacrylate) (PMMA), polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly (1,4-isopropylidene diphenylene carbonate), vinylidene chloride, acrylonitrile copolymer, vinyl chloride-diethyl fumerale copolymer, silicone rubbers, ethylene-propylene rubber, silicone-carbonate copolymers, vinylidene chloride-vinyl chloride copolymer, vinyl chloride-acrylonitrile copolymer and vinylidene chloride-acrylonitride copolymer, polycarbonate, polyurethane, thermoplastic elastomers (TPE) (such as e.g. SEBS (styrene-ethylene-butylene-styrene), SBS (styrene-butadiene-styrene), MBM (methylmethacrylate-butadiene-methylmethacrylate)), or combinations thereof.

The degree of cross-linking in the polymer may be advantageously used to regulate the drug release rates from the polymeric matrix core. For example, a polymer with high degree of cross-linking will release the drug at a lower rate than a polymer with a lesser degree of cross-linking.

In an embodiment, the polymeric matrix core comprises a polymer selected from the group consisting of ethylene-co-vinylacetate (EVA), poly(dimethylsiloxane) (PDMS), polypropylene (PP), polyethylene (PE), preferably high density polyethylene (HDPE), (plasticized) polyethylene terephthalate (PET), poly(methyl methacrylate) (PMMA), polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4-isopropylidene diphenylene carbonate), vinylidene chloride, acrylonitrile copolymer, vinyl chloride-diethyl fumerale copolymer, silicone rubbers, ethylene-propylene rubber, silicone-carbonate copolymers, vinylidene chloride-vinyl chloride copolymer, vinyl chloride-acrylonitrile copolymer and vinylidene chloride-acrylonitride copolymer, polycarbonate, polyurethane, thermoplastic elastomers (TPE) (such as e.g. SEBS (styrene-ethylene-butylene-styrene), SBS (styrene-butadiene-styrene), MBM (methylmethacrylate-butadiene-methylmethacrylate)), or combinations thereof.

In a particular embodiment, the polymeric matrix core comprises a polymer selected from the group consisting of ethylene-co-vinylacetate (EVA), poly(dimethylsiloxane) (PDMS), or combinations thereof.

In a particular embodiment, the polymeric matrix core comprises a polymer selected from the group consisting of polyethylene (PE), preferably high density polyethylene (HDPE), poly(methyl methacrylate) (PMMA), and combinations thereof.

The polymeric matrix core of the sustained release intraocular drug delivery device of the present invention also comprises at least one therapeutic agent. The polymeric matrix core of the sustained release intraocular drug delivery device of the present invention may comprise from 0.1 to 50% by weight of the at least one therapeutic agent based on the total weight of polymeric matrix material. Preferably, the polymeric matrix core comprises from 1.0 to 50% or 5.0 to 50% by weight of said at least one therapeutic agent based on the total weight of polymeric matrix material.

In particular embodiments, the polymeric matrix comprises a polymer selected from the group consisting of polyethylene (PE), preferably high density polyethylene (HDPE), poly(methyl methacrylate) (PMMA), and combinations thereof, wherein at least one therapeutic agent is dispersed throughout said polymer (i.e. wherein at least one therapeutic agent is mixed with said polymer).

The matrix core or polymeric matrix core or the sustained release intraocular drug delivery device of the present invention may also comprise a supporting structure to increase the flexibility of said device. Preferably, said supporting structure is a filament. More preferably, said structure is a metallic filament.

In an embodiment, the matrix core or polymeric matrix core of the sustained release intraocular drug delivery device of the present application comprises a metallic filament.

The sustained release intraocular drug delivery device of the present application also comprises a "polymeric coating" completely surrounding the matrix material, which further regulates the release of the therapeutic agent contained in the polymeric matrix material. Said polymeric coating comprises a polymer, which is insoluble and inert in ocular fluids (i.e. biocompatible), while at the same time it is not absorbed or degraded by the eye tissues. Preferably, the polymer of said polymeric coating is permeable to the therapeutic agent.

Polymers suitable for the polymeric coating include, for example: ethylene-co-vinylacetate (EVA), poly(dimethylsiloxane) (PDMS), polypropylene (PP), polyethylene (PE), preferably high density polyethylene (HDPE), (plasticized) polyethylene terephthalate, poly(methyl methacrylate) (PMMA), crosslinked polyvinyl alcohol, polyolefins or polyvinyl chlorides or cross-linked gelatins; regenerated, insoluble, nonerodible cellulose, acylated cellulose, esterified celluloses, cellulose acetate propionate, cellulose acetate butyrate, cellulose acetate phthalate, cellulose acetate diethyl-aminoacetate; polyurethanes, polycarbonates, and microporous polymers formed by co-precipitation of a polycation and a polyanion modified insoluble collagen, or combinations thereof.

In an embodiment, the polymeric coating comprises a polymer selected from the group consisting of ethylene-co-vinylacetate (EVA), poly(dimethylsiloxane) (PDMS), polypropylene (PP), polyethylene (PE), preferably high density polyethylene (HDPE), (plasticized) polyethylene terephthalate, poly(methyl methacrylate) (PMMA), crosslinked polyvinyl alcohol, polyolefins or polyvinyl chlorides or cross-linked gelatins; regenerated, insoluble, nonerodible cellulose, acylated cellulose, esterified celluloses, cellulose acetate propionate, cellulose acetate butyrate, cellulose acetate phthalate, cellulose acetate diethyl-aminoacetate; polyurethanes, polycarbonates, and microporous polymers formed by co-precipitation of a polycation and a polyanion modified insoluble collagen, or combinations thereof.

In a particular embodiment, the polymeric coating comprises ethylene-co-vinylacetate (EVA).

In a particular embodiment, the coating comprises a polymer selected from the group consisting of polyethylene (PE), preferably high density polyethylene (HDPE), poly(methyl methacrylate) (PMMA), and combinations thereof.

The degree of cross-linking in the polymer selected for the polymeric coating may be advantageously used to regulate the drug release rates from the intraocular drug delivery device. For example, a polymer with high degree of cross-linking will release the drug at a lower rate than a polymer with a lesser degree of cross-linking.

In embodiments, a sustained release intraocular drug delivery device is provided comprising:
(a) a matrix core comprising a polymer selected from the group consisting of polyethylene (PE), preferably high density polyethylene (HDPE), poly(methyl methacrylate) (PMMA), and combinations thereof, wherein at least one therapeutic agent, preferably timolol, is mixed with said polymer, and (b) a coating completely surrounding said matrix, which coating comprises a polymer selected from the group consisting of polyethylene (PE), preferably high density polyethylene (HDPE), poly(methyl methacrylate) (PMMA), and combinations thereof,
wherein said sustained release intraocular drug delivery device is configured for the sulcus of the eye.

In particular embodiments, the sustained release intraocular drug delivery device comprises:
(a) a matrix core comprising polyethylene (PE), preferably high density polyethylene (HDPE), wherein at least one therapeutic agent, preferably timolol, is mixed with said PE, and
(b) a coating comprising polyethylene (PE), preferably high density polyethylene (HDPE).

In particular embodiments, the sustained release intraocular drug delivery device comprises:
(a) a matrix core comprising polyethylene (PE), preferably high density polyethylene (HDPE), wherein at least one therapeutic agent, preferably timolol, is mixed with said PE, and
(b) a coating comprising poly(methyl methacrylate) (PMMA).

In particular embodiments, the sustained release intraocular drug delivery device comprises:
(a) a matrix core comprising poly(methyl methacrylate) (PMMA), wherein at least one therapeutic agent, preferably timolol, is mixed with said PMMA, and
(b) a coating comprising poly(methyl methacrylate) (PMMA).

In particular embodiments, the sustained release intraocular drug delivery device comprises:
(a) a matrix core comprising poly(methyl methacrylate) (PMMA), wherein at least one therapeutic agent, preferably timolol, is mixed with said PMMA, and,
(b) a coating comprising polyethylene (PE), preferably high density polyethylene (HDPE).

In particular embodiments, the sustained release intraocular drug delivery device comprises:
(a) a matrix core comprising poly(methyl methacrylate) (PMMA), wherein at least one therapeutic agent, preferably timolol, is mixed with said PMMA, and
(b) a coating comprising ethylene-co-vinylacetate (EVA).

In particular embodiments, the sustained release intraocular drug delivery device comprises:
(a) a matrix core comprising polyethylene (PE), preferably high density polyethylene (HDPE), wherein at least one therapeutic agent, preferably timolol, is mixed with said PE, and
(b) a coating comprising ethylene-co-vinylacetate (EVA).

In particular embodiments, the sustained release intraocular drug delivery device comprises:
(a) a matrix core comprising poly(methyl methacrylate) (PMMA), wherein at least one therapeutic agent, preferably timolol, is mixed into said PMMA, and
(b) a coating comprising polypropylene (PP).

In particular embodiments, the sustained release intraocular drug delivery device comprises:
(a) a matrix core comprising polyethylene (PE), preferably high density polyethylene (HDPE), wherein at least one therapeutic agent, preferably timolol, is mixed with said PE, and
(b) a coating comprising polypropylene (PP).

The dimensions of the sustained release intraocular drug delivery device of the present application are an important parameter to take into account, considering the limited anatomical space that the eye constitutes. The device should be configured for the sulcus of the eye. Larger devices require complex surgery to both implant and remove; the increased complexity may result in complications, longer healing or recovery periods, and potential side effects. The expression "configured for the sulcus of the eye" should therefore, when read in the definition of the device according to the invention, be seen as a member that has the shape and dimensions allowing it to be inserted or implanted into the sulcus of the eye, which has uniform dimensions throughout the human population (a diameter of 11±0.37 mm, Davis et al, Cornea 1991).

The sustained release intraocular drug delivery device of the present application has an annular shape, with a cross sectional diameter that may range from 0.10 to 0.80 mm. In an embodiment, the cross sectional diameter of the sustained release intraocular drug delivery device of the present application ranges from 0.20 to 0.50 mm. In yet another embodiment, the cross sectional diameter of the sustained release intraocular drug delivery device of the present application ranges from 0.30 to 0.45 mm. In a preferred embodiment, the cross-sectional diameter of the sustained release intraocular drug delivery device of the present application ranges from 0.33 to 0.38 mm. Said annular shape also comprises annular segments ranging from 90 to 360° of the ring. Preferably, said annular segment ranges from 180 to 360°, more preferably from 300 to 360°, depending on the volume needed to accommodate the therapeutically effective amount of drug or therapeutic compound.

Figure 2:
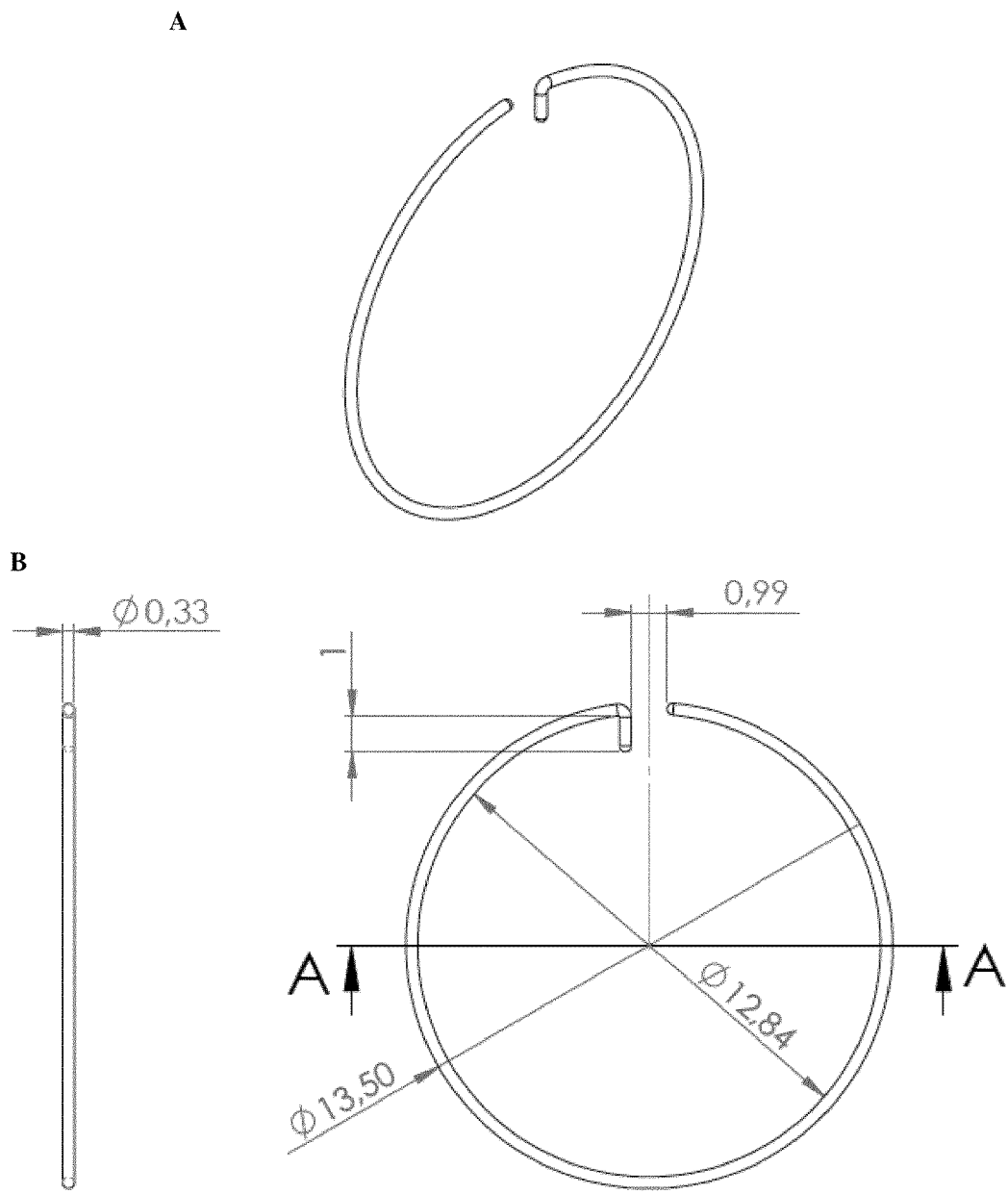
FIG. 2A, shows a three-dimensional representation of the sustained release intraocular drug delivery device, according to an embodiment of the present application.
FIG. 2B, shows a side view of the polymeric matrix of the sustained release intraocular drug delivery device, according to an embodiment of the present application.

In embodiments, the sustained release intraocular drug delivery device of the present application has an annular shape, with an external diameter comprised between 5.0 and 15.0 mm, preferably between 10.0 and 15.0 mm, more preferably between 13.0 and 14.0 mm, such as about 13.5 mm (cf. FIG. 2).

The skilled person will therefore be able to envisage that the dosage and duration of the therapy may be adjusted by changing the angle of the annular segments of the ring. For example, an annular segment with a 90° angle will be smaller than an annular segment with a 300° angle; thus the smaller segment would contain a smaller dose or would be adept for a shorter therapy or a lower dose. Likewise, an annular segment with a 180° angle will typically comprise about half the dose of an annular segment with a 360° angle.

The length of sustained release intraocular drug delivery device of the present application may also be adapted to accommodate the therapeutically effective amount of drug or therapeutic compound; thus the length of the sustained release intraocular drug delivery device of the present application may range from 5.0 to 40.0 mm, such as from 5.0 to 10 mm, 5.0 to 14.0 mm, 5.0 to 20 mm, 5.0 to 25.0 mm, 5.0 to 30 mm, or 5.0 to 35 mm. Preferably, the length of the sustained release intraocular drug delivery device of the present application is calculated based on the external diameter outlined above (cf. FIG. 2). As an example, a length of about 35.0 to 40.0 mm corresponds to an annular segment of about 350 to 360° if the device has an external diameter of about 13.5 mm. An annular segment of about 180° (about half of the ring), will in such a case typically have a length of 17.5 mm to 20.0 mm.

In embodiments, the device as described herein has a length comprised between 5.0 and 50.0 mm, such as between 10.0 and 40.0 mm.

The skilled person will therefore be able to envisage that the dosage and duration of the therapy may be further adjusted by changing the length of the device. Thus, a device of, for example 10.0 mm, may contain a smaller dose or may be adept for a shorter therapy or a lower dose, than a device, of for example 14.0 mm. Likewise, a device of 7.0 mm will typically comprise about half the dose than a device of 14.0 mm will contain.

Changing the length or angle of the annular sustained release device is hence an easy way to produce devices with a different dosage of the active ingredient, without the need of manufacturing new moulds or without the need for changing the matrix core composition.

Furthermore, the cross-sectional dimensions of the polymeric matrix core of the present sustained release intraocular drug delivery device also determine the amount of therapeutic agent that said device contains, and therefore, also the dosage and duration of the therapy. Thus, the polymeric matrix core of the present sustained release intraocular drug delivery device of the present application has a rod shape, with a cross-sectional diameter that may range from 0.05 mm to 0.48 mm. In yet another embodiment, the cross-sectional diameter of the polymeric matrix core ranges from 0.11 to 0.19 mm. In a preferred embodiment, the cross-sectional diameter of the polymeric matrix core ranges from 0.13 to 0.18 mm (cf. FIG. 1). The maximal cross-section is a cross-section that still allows the device to be placed in the sulcus of the human eye, preferably the human adult eye, while the minimal cross-section is a cross-section that still enables stability of the device and ease of manipulation.

FIG. 1 shows a schematic representation of the polymeric matrix of the intraocular drug delivery device, according to an embodiment of the present application, wherein said polymeric matrix has a cross-sectional diameter of 0.13 mm, and said polymeric matrix has an annular shape, comprising an annual compliant segment. Said annual compliant segment exhibits an angle of 355°.

Since the polymeric coating further regulates the release of the therapeutic agent contained in the matrix material, its dimensions also aid in determining the dosage regimen and duration of the therapy. Thus the polymeric coating may have a thickness ranging from 0.05 to 0.32 mm. In yet another embodiment, the polymeric coating has a thickness ranging from 0.08 to 0.29 mm. In another embodiment, the polymeric coating has a thickness ranging from 0.11 to 0.20 mm. In an embodiment, the polymeric coating has a thickness ranging from 0.13 to 0.18 mm (cf. FIG. 2).

In another embodiment, the polymeric coating is a polymeric membrane.

In an embodiment, said polymeric coating is a polymeric membrane with a thickness ranging from 0.05 to 0.32 mm, such as from 0.05 to 0.20 mm.

In an embodiment, the intraocular drug delivery device according to embodiments described herein, wherein said polymeric coating is a polymeric membrane with a thickness ranging from 0.12 to 0.32 mm.

The materials used in the intraocular drug delivery device according to the invention are selected specifically to ensure that said device forms a compliant annular segment. That is, the annular segment can be straightened by applying force, but will return to its original annular shape when force is no longer applied. This is important, since this enables the simple insertion of the device into the eye, i.e. by temporarily linearising it, after which is returns to its original shape and follows the anatomy of the sulcus of the eye after being inserted. The particular dimensions of the sustained release intraocular drug delivery device of the present application allow for its ease of insertion into the eye.

The materials are further selected to ensure that the device is stiff or rigid enough to allow implantation. With "stiffness" or "rigidity" is meant herein the extent to which an object resists deformation in response to an applied force.

More particularly, the materials are selected so as to ensure a Young's modulus of at least at least about 200 MPa, such as at least about 210 MPa, 220 MPa, 230 MPa or 240 MPa, preferably at least about 250 MPa, even more preferably at least about 300 MPa, as determined at room temperature (about 21° C.).

Accordingly, in embodiments, the intraocular drug delivery device as taught herein has a Young's modulus of at least about 200 MPa, such as at least about 210 MPa, 220 MPa, 230 MPa or 240 MPa, preferably at least about 250 MPa, even more preferably at least about 300 MPa, as determined at room temperature (about 21° C.).

"Young's modulus" or "tensile modulus" or "elastic modulus" is defined herein as a measure of the stiffness of an object.

Also preferably, the materials are selected so as to ensure strength at break of at least 5 MPa, preferably at least 10 MPa, more preferably at least 15 MPa, as measured at room temperature (about 21° C.).

"Ultimate tensile strength (UTS)" or "tensile strength (TS)" or "ultimate strength" or "strength at break" is the maximum stress that a material or an object can withstand while being stretched or pulled before failing or breaking. Some materials will break sharply, without plastic deformation, in what is called a brittle failure. Others, which are more ductile will experience some plastic deformation and possibly necking before fracture.

Also preferably, the materials are selected so as to ensure an elongation at break of at least 5% (relative to the initial length), preferably at least 10% (relative to the initial length), as determined at room temperature (about 21° C.).

As used herein "elongation at break" denotes the ratio between changed length and initial length after breakage of an object.

Figure 10:
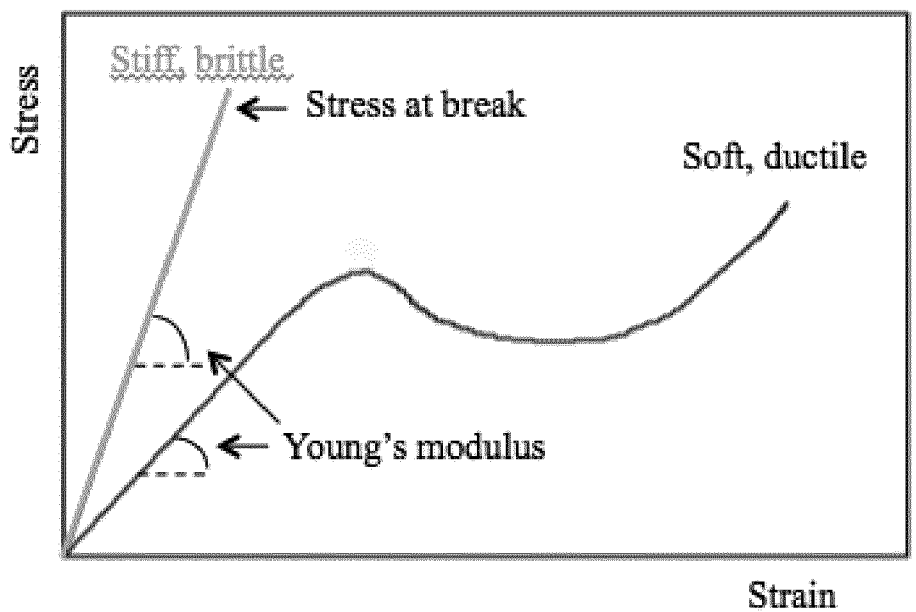
FIG. 10 shows how Young's modulus and stress at break/flow of a material can be determined from a tensil curve of the material.

Young's modulus, UTS, and elongation at break can be determined by performing a tensile test according to the standard ISO 527 and recording the engineering stress (force per unit area) versus strain (ratio of deformation over initial length). The ratio of the stress along an axis to the strain along that axis in the linear region of the tensile curve is the Young's modulus (FIG. 10). The highest point of the stress-strain curve is the UTS (FIG. 10).

Typically, the testing involves pulling a sample with a tensometer, thereby gradually increasing force until the sample breaks. For example, a tensile test can be performed using an electromechanical tensometer (e.g. Instron 5566, Elancourt, France). The samples are mounted between holders (e.g. Pneumatic Action grips, Elancourt, France) and pulled at a rate of 5 mm/min at room temperature (about 21° C.). Young's modulus (in MPa) and strain at break (%) can be automatically calculated by the Instron software (Bluehill 2, Elancourt, France). To obtain Young's modulus, the software calculates the slope of each stress-strain curve in its elastic deformation region (the elastic deformation region of each curve can be manually delimitated by moving cursors).

The device may be directly introduced through a clear self-sealing corneal incision (<2.0 mm) between the iris plane and the intraocular pseudophakic lens or the natural lens; or inserted with the aid of a micro inserter device such as the InjectorRing®, which permits the precise insertion of the device in the area of the eye known as the sulcus. Both procedures may be performed under topical anesthesia, and after pupil dilation. Viscoelastic material might be injected during the procedure to help the correct positioning of the implant in the sulcus, with micromanipulators. Once placed in correct position, the implant may remain in position permanently, may be exchanged for another implant, or may be removed during a second procedure.

Figure 7:
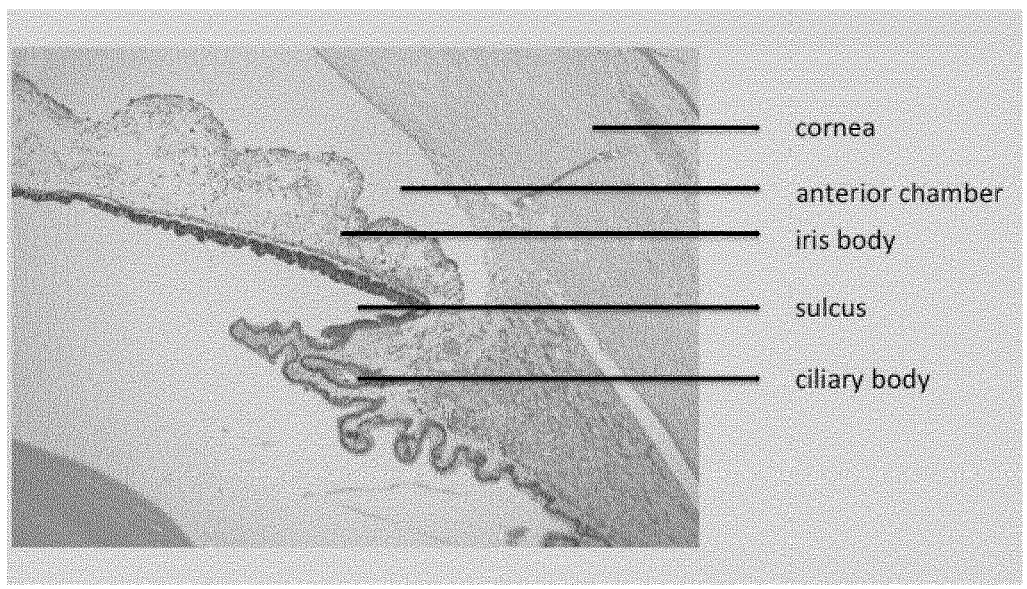
FIG. 7 shows a micrograph of a human eye, showing the site of insertion of the intraocular drug delivery device into the sulcus (Petermeier K. et al; J Cataract Refract. Surg. Vol. 38:986-991, 2012)

As used herein, the term "sulcus of the eye" refers to the anatomic eye component corresponding to the space formed by the posterior surface of the iris and the internal and slightly anterior projection of the anterior-most ciliary processes (Smith S G, et al; J. Cataract Refract. Surg. 13:543, 1987) (see FIG. 7).

The use of the sulcus of the eye as insertion point for the sustained release intraocular drug delivery device of the present application is particularly advantageous, since it eliminates the risk to initiate fibrotic processes in the patient, therefore minimizing rejection of the device and ensuring the possibility of removing and/or replacing the device after a certain period of time.

In particular embodiments, the sustained release intraocular drug delivery device of the present application comprises a tag or protrusion to ease its manipulation during insertion or removal of said device. Said tag or protrusion enables the user to grab it with e.g. using a micro inserter or tweezer, for easy insertion into the eye or removal from the eye. Preferably, said tag or protrusion measures at least 1.0 mm, FIG. 2 shows a schematic representation of the drug delivery device comprising said tag, according to an embodiment of the present application.

Since the sustained release intraocular drug delivery devices of the present application are formed of materials that are insoluble and inert in ocular fluids, and not absorbed or degraded by the eye tissues, they retain their shape and integrity during the course of the needed therapy to serve as a drug reservoir for continuously administering drug to the eye and the surrounding tissues at a rate that is not affected by dissolution or erosion of the material. Thus, the sustained release intraocular drug delivery device of the present application may provide a complete ophthalmic dosage regime for a prolonged period of time, which may be weeks, months or even years as desired. Preferably, the sustained release intraocular drug delivery device of the present application provides a complete ophthalmic dosage regime for one to two years, in order to reduce or limit the discomfort for the patient as much as possible. More preferably, the sustained release intraocular drug delivery device of the present application provides a complete ophthalmic dosage regime for up to five years.

The sustained release intraocular drug delivery device of the present application, on termination of the desired therapeutic program, may then be removed from its intraocular location in the sulcus of the eye. The time-dependent delivery of the at least one therapeutic agent to the eye by the sustained release intraocular drug delivery device of the present application, makes it possible to maximize the pharmacological and physiological effects of the treatment.

Since the sustained release intraocular drug delivery device of the present application requires intervention only for initiation and termination of the therapy (i.e. removal of the device), patient compliance issues during the treatment regiment are mostly eliminated.

The device according to the present application, contains at least one therapeutic agent selected from the group consisting of antibiotic agents, antibacterial agents, antiviral agents, prostaglandin analogues, anti-glaucoma agents, antiallergenic agents, anti-inflammatory agents, anti-angiogenesis agents, immune system modifying agents, anti-cancer agents, antisense agents, antifungal agents, myotic and anticholinesterase agents, mydriatic agents, differentiation modulator agents, sympathomimetic agents, anaesthetic agents, vasoconstrictive agents, vasodillatory agents, decongestants, cell transport/mobility impending agents, polypeptides and protein agents, steroidal agents, carbonic anhydrase inhibitor agents, polycations, polyanions, and lubricating agents.

The therapeutic agents and drugs that can be delivered by the sustained release intraocular drug delivery device of the present application include, for example: antibiotic agents such as fumagillin analogs, minocycline, fluoroquinolone, cephalosporin antibiotics, herbimycon A, tetracycline, chlortetracycline, bacitracin, neomycin, polymyxin, gramicidin, oxytetracycline, chloramphenicol, gentamicin and erythromycin; antibacterial agents such as sulfonamides, sulfacetamide, sulfamethizole, sulfoxazole, nitrofurazone, and sodium propionate; antiviral agents such as idoxuridine, famvir, trisodium phosphonoformate, trifluorothymidine, acyclovir, ganciclovir, DDI and AZT, protease and integrase inhibitors; prostaglandin analogues such as latanoprost, travoprost, unoprostone and bimatoprost; anti-glaucoma agents such as beta blockers (timolol, betaxolol, atenolol), prostaglandin analogues, hypotensive lipids, and carbonic anhydrase inhibitors; antiallergenic agents such as antazoline, methapyriline, chlorpheniramine, pyrilamine and prophenpyridamine; antiinflammatory agents such as hydrocortisone, leflunomide, dexamethasone phosphate, fluocinolone acetonide, medrysone, methylprednisolone, prednisolone phosphate, prednisolone acetate, fluorometholone, betamethasone, triamcinolone acetonide, adrenalcortical steroids and their synthetic analogues, and 6-mannose phosphate; anti-angiogenesis agents including those that can be potential anti-choroidal neovascularization agents such as 2-methoxyestradiol and its analogues (e.g., 2-propynl-estradiol, 2-propenyl-estradiol, 2-ethoxy-6-oxime-estradiol, 2-hydroxyestrone, 4-methoxyestradiol), VEGF antagonists such as VEGF antibodies (such as bevacizumab, ranibizumab, aflibercept) and VEGF antisense, angiostatic steroids (e.g., anecortave acetate and its analogues, 17-ethynylestradiol, norethynodrel, medroxyprogesterone, mestranol, androgens with angiostatic activity such as ethisterone); immune system modifying agents such as cyclosporine A, Prograf (tacrolimus), macrolide immunosuppressants, mycophenolate mofetil, rapamycin, and muramyl dipeptide, and vaccines; anti-cancer agents such as 5-fluoroucil, platinum coordination complexes such as cisplatin and carboplatin, adriamycin, antimetabolites such as methotrexate, anthracycline antibiotics; antisense agents such as fomivirsen; antifungal agents such as fluconazole, amphotericin B, liposomal amphotericin B, voriconazole, imidazole-based antifungals, triazole antifungals, echinocandin-like lipopeptide antibiotics; myotic and anticholinesterase agents such as pilocarpine, eserine salicylate, carbachol, diisopropyl fluorophosphate, phospholine iodine, and demecarium bromide; mydriatic agents such as atropine sulfate, cyclopentane, homatropine, scopolamine, tropicamide, eucatropine, and hydroxyamphetamine; differentiation modulator agents; sympathomimetic agents such as epinephrine; anesthetic agents such as lidocaine and benzodiazepam; vasoconstrictive agents such as pseudoephedrine and phenylephrine; vasodillatory agents such as tolazoline, nicotinic acid, nicotinyl alcohol and nylidrin; decongestants such as naphazoline, phenylephrine, tetrahydrozoline and exymetazoline; polypeptides and protein agents such as angiostatin, endostatin, matrix metalloproteinase inhibitors, platelet factor 4, interferon-gamma, insulin, growth hormones, insulin related growth factor, heat shock proteins, humanized anti-IL-2 receptor mAb (daclizumab), etanercept, mono and polyclonal antibodies, cytokines, antibody to cytokines; steroidal agents such as triamcinolone, dexamethasone, clobetasol, betamethasone, and halometasone; cell transport/mobility impending agents such as colchicine, vincristine, cytochalasin B; carbonic anhydrase inhibitor agents such as acetazolamide, brinzolamide, dorzolamide and methazolamide; polycations and polyanions such as suramine and protamine; and lubricating agents.

This listing of therapeutic agents is illustrative, and not exhaustive, since the skilled person will appreciate that any drug that could be used for treatment through intraocular administration could be applied using the intraocular device according to the present invention.

Additionally, the intraocular drug delivery device of the present application may further comprise one or more pharmaceutically acceptable carriers or excipients.

The term "pharmaceutically acceptable carrier" or "pharmaceutically acceptable excipient" as used herein, means any material or substance with which the therapeutic agent may be formulated. Suitable pharmaceutical carriers for use in the said pharmaceutical compositions and their formulation are well known to those skilled in the art. There is no particular restriction to their selection within the present application Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The at least one therapeutic agent may be formulated as to further affect the release rate from the sustained release intraocular drug delivery device. For example, the at least one therapeutic agent may be microencapsulated (coated with a material that delays the dispersion of the therapeutic agent), complexed with an ion exchange resin, or embedded in a porous matrix. When more than one therapeutic agent is used, each agent may be formulated separately, such that each of said agents exhibits different release rates from the sustained release intraocular drug delivery device (Tomaro-Duchesneau, C., et al, J. Pharmaceutics, 2013, Article ID 103527, 19 pages; Srikanth, M. V. et al, J. Sci. Res. 2(3), 597-611; Gruber, M. F., et al; J. Coll. Interf. Sci., 395 (2013) 58-63).

A particular embodiment the present application also encompasses the device according to embodiments described herein, wherein at least one therapeutic agent is selected from the group consisting of prostaglandin analogues, anti-glaucoma agents, anti-inflammatory agents, anti-angiogenesis compounds, immune system modifying agents.

In a preferred embodiment, the at least one therapeutic agent is selected from the group consisting of bevacizumab, ranibizumab, aflibrcept, timolol, latanoprost dorzolamide, triamcinolone, dexamethasone or cyclosporin. In a particularly preferred embodiment, the at least one therapeutic agent is timolol.

Another aspect of the present application relates to a therapeutic agent for use in the treatment of ocular diseases, wherein said therapeutic agent is administered in a sustained release intraocular drug delivery device according to embodiments described herein, and wherein said sustained release intraocular drug delivery device is inserted into the sulcus of the eye.

Another aspect of the present application relates to a therapeutic agent selected from the group consisting of bevacizumab, ranibizumab, aflibercept, timolol, latanoprost, dorzolamide, triamcinolone, dexamethasone or cyclosporine for use in the treatment of ocular diseases, wherein said therapeutic agent is administered in a sustained release intraocular drug delivery device according to embodiments described herein, and wherein said sustained release intraocular drug delivery device is inserted into the sulcus of the eye.

Another aspect of the present application relates to a therapeutic agent selected from the group consisting of bevacizumab, ranibizumab, timolol, latanoprost or cyclosporine for use in the treatment of ocular diseases, wherein said therapeutic agent is administered in a sustained release intraocular drug delivery device according to embodiments described herein, and wherein said sustained release intraocular drug delivery device is inserted into the sulcus of the eye.

As used herein, the term "ocular disease" refers to any condition which affects or involves the eye or one of the parts or regions of the eye. Broadly speaking, the eye includes the eyeball and the tissues and fluids which constitute the eyeball, the periocular muscles (such as the oblique and rectus muscles) and the portion of the optic nerve which is within or adjacent to the eyeball.

An anterior ocular disease is any condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular disease primarily affects or involves the conjunctiva, the cornea, the anterior chamber, the iris, the lens or the lens capsule and blood vessels and nerve which vascularize or innervate an anterior ocular region or site. Examples of anterior ocular diseases which can be treated using the sustained release intraocular drug delivery device of the present application include aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma may also be considered to be an anterior ocular disease because a clinical goal of glaucoma treatment can be to reduce hypertension, caused by excess of aqueous fluid in the anterior chamber of the eye (i.e. reduce intraocular pressure).

A posterior ocular disease is any condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site. Examples of posterior ocular diseases which can be treated using the sustained release intraocular drug delivery device of the present application include acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma may be considered a posterior ocular condition because the therapeutic goal is to prevent the loss of or reduce the occurrence of loss of vision due to damage to or loss of retinal cells or optic nerve cells (i.e. neuroprotection).

As used herein, the terms "treat", "treating", or "treatment", refer to reduction, resolution or prevention of an ocular disease, ailment or condition, or to promote healing of injured or damaged ocular tissue. A treatment is usually effective to reduce at least one symptom of an ocular disease, ailment or condition.

The term "therapeutically effective amount" as used herein, refers to the level or amount of agent needed to treat an ocular disease, or reduce or prevent ocular injury or damage without causing significant negative or adverse side effects to the eye or a region of the eye. In view of the above, a therapeutically effective amount of a therapeutic agent, is an amount that is effective in reducing at least one symptom of an ocular disease, condition or ailment.

A third aspect of the present application deals with a method of treating ocular diseases comprising administering a therapeutically effective amount of a compound for use in the treatment of ocular diseases, wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprising administering a therapeutically effective amount of a compound selected from the group consisting of bevacizumab, ranibizumab, aflibercept, timolol, latanoprost, dorzolamide, triamcinolone, dexamethasone or cyclosporine, wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprises administering a therapeutically effective amount of bevacizumab wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprises administering a therapeutically effective amount of ranibizumab wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprises administering a therapeutically effective amount of aflibercept wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprises administering a therapeutically effective amount of timolol wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprises administering a therapeutically effective amount of latanoprost wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprises administering a therapeutically effective amount of dorzolamide wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprises administering a therapeutically effective amount of triamcinolone wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprises administering a therapeutically effective amount of dexamethasone wherein said compound is administered in a sustained release intraocular drug delivery device according to embodiments described herein, and wherein said sustained release intraocular drug delivery device is inserted into the sulcus of the eye, such that the ocular disease is treated.

In an embodiment the method of treating ocular diseases comprises administering a therapeutically effective amount of cyclosporine wherein said compound is administered in a sustained release intraocular drug delivery device according to embodiments described herein, and wherein said sustained release intraocular drug delivery device is inserted into the sulcus of the eye, such that the ocular disease is treated.

The sustained release intraocular drug delivery devices described herein can be manufactured by molding or laser cutting.

A fourth aspect of the present application provides a process for preparing a sustained release intraocular drug delivery device according to the first aspect of the present application, comprising:
  mixing the at least one therapeutic agent with an insoluble and inert polymer;
  molding and/or extruding said mixture to afford a polymeric matrix core; and,
  providing the resulting polymeric matrix core with a polymeric coating.

The at least one therapeutic agent may be mixed with an insoluble and inert polymer to provide a homogeneous mixture. The mixing step may be performed with a spatula or other suitable mixing instruments. Alternatively, the mixing step may be performed with a blender.

In a particular embodiment of the present application, the mixture of the insoluble and inert polymer and the at least one therapeutic agent is placed in a mold, and said mold is heated, to obtain a polymeric matrix core.

In an embodiment, said heating of the mold is performed at a temperature ranging from 50 to 150° C.; preferably, the heating of the mold is performed at a temperature ranging from 80 to 120° C.

In another embodiment, said mold is heated for a period ranging between 0.5 and 50 minutes; preferably, said mold is heated for a period ranging between 1 minute and 40 minutes; more preferably, said mold is heated for a period ranging between 2 minutes and 30 minutes.

In another embodiment, said heating of the mold is performed at a temperature ranging from 80 to 120° C., for a period ranging between 2 minutes and 30 minutes.

Alternatively, when the mixture of the insoluble and inert polymer and the at least one therapeutic agent is placed in the mold, and said mold is heated, pressure may be also applied to the mold, to afford the polymeric matrix core. In a particular embodiment of the present application, the mixture of the insoluble and inert polymer and the at least one therapeutic agent is placed in a mold, and said mold is heated under pressure, to obtain a polymeric matrix core.

In an embodiment, said heating of the mold under pressure is performed at a temperature ranging from 50 to 150° C.; preferably, the heating of the mold is performed at a temperature ranging from 80 to 120° C.

In another embodiment, said mold is heated under pressure for a period ranging between 0.5 and 50 minutes; preferably, said mold is heated under pressure for a period ranging between 1 minute and 40 minutes; more preferably, said mold is heated under pressure for a period ranging between 2 minutes and 30 minutes.

In another embodiment said mold is heated under pressure at a pressure ranging from 2.5 to 10 N; preferably, said mold is heated under pressure at a pressure ranging from 3.5 to 9 N; more preferably, said mold is heated under pressure at a pressure ranging from 5 to 7.5 N.

In another embodiment, said heating of the mold under pressure is performed at a temperature ranging from 80 to 120° C., for a period ranging between 2 minutes and 30 minutes and at a pressure ranging from 5 to 7.5 N.

In an embodiment of the present application, the process for preparing a sustained release intraocular drug delivery device according to the first aspect of the present application comprises:
mixing the at least one therapeutic agent with an insoluble and inert polymer;
molding said mixture to afford a polymeric matrix core; and,
providing the resulting polymeric matrix core with a polymeric coating.

In another particular embodiment, the mixture of the insoluble and inert polymer and the at least one therapeutic agent is extruded to afford a polymeric matrix core.

Extrusion methods include both extrusion (i.e. the process in which a polymeric material is melted and formed into a continuous profile) and co-extrusion methods (co-extrusion is the extrusion of multiple layers of material simultaneously).

In another particular embodiment, the mixture of the insoluble and inert polymer and the at least one therapeutic agent is co-extruded to afford a polymeric matrix core.

When using extrusion/co-extrusion methods, the polymer and at least one therapeutic agent may be chosen so as to be stable at the temperatures required for manufacturing, usually at least about 85° C. Extrusion/co-extrusion methods use temperatures of about 50° C. to about 170° C. more preferably about 65° C. to about 130° C. The polymer matrix core may be produced by first bringing the temperature of the extruder to about 60° C. to about 150° C. for drug/polymer mixing, such as about 120° C., for a time period of about 0 to 1 hour, 0 to 30 minutes, or 5 to 15 minutes. For example, a time period may be about 10 minutes, preferably about 0 to 5 min. Preferably, the mixture of the insoluble and inert polymer and the at least one therapeutic agent is extruded or co-extruded at a temperature of about 50° C. to about 170° C., such as about 120° C., to form polymer sheets with a thickness of at least 130 μm.

The resulting polymer sheets may be then placed in a mold and heated, to obtain a polymeric matrix core. In a particular embodiment of the present application, the polymer sheet with a thickness of at least 130 μm is placed in a mold, and said mold is heated to obtain a polymeric matrix core.

In an embodiment, said heating of the mold is performed at a temperature ranging from 50 to 150° C.; preferably, the heating of the mold is performed at a temperature ranging from 80 to 120° C.

In another embodiment, said mold is heated for a period ranging between 0.5 and 50 minutes; preferably, said mold is heated for a period ranging between 1 minute and 40 minutes; more preferably, said mold is heated for a period ranging between 2 minutes and 30 minutes.

In another embodiment, said heating of the mold is performed at a temperature ranging from 80 to 120° C., for a period ranging between 2 minutes and 30 minutes.

Alternatively, when the polymer sheet with a thickness of at least 130 μm is placed in the mold, and said mold is heated, pressure may be also applied to the mold, to afford the polymeric matrix core. In a particular embodiment of the present application, the polymer sheet with a thickness of at least 130 μm is placed in a mold, and said mold is heated under pressure, to obtain a polymeric matrix core.

In an embodiment, said heating of the mold under pressure is performed at a temperature ranging from 50 to 150° C.; preferably, the heating of the mold is performed at a temperature ranging from 80 to 120° C.

In another embodiment, said mold is heated under pressure for a period ranging between 0.5 and 50 minutes; preferably, said mold is heated under pressure for a period ranging between 1 minute and 40 minutes; more preferably, said mold is heated under pressure for a period ranging between 2 minutes and 30 minutes.

In another embodiment said mold is heated under pressure at a pressure ranging from 2.5 to 10 N; preferably, said mold is heated under pressure at a pressure ranging from 3.5 to 9 N; more preferably, said mold is heated under pressure at a pressure ranging from 5 to 7.5 N.

In another embodiment, said heating of the mold under pressure is performed at a temperature ranging from 80 to 120° C., for a period ranging between 2 minutes and 30 minutes and at a pressure ranging from 5 to 7.5 N.

In an embodiment of the present application, the process for preparing a sustained release intraocular drug delivery device according to the first aspect of the present application comprises:
mixing the at least one therapeutic agent with an insoluble and inert polymer;

extruding and molding said mixture to afford a polymeric matrix core; and, providing the resulting polymeric matrix core with a polymeric coating.

In a particular embodiment of the present application, the step of providing the resulting polymer matrix core with a polymeric coating is performed by covering said resulting polymeric matrix core with a polymeric membrane in a mold, and heating said mold.

In an embodiment, said heating of the mold is performed at a temperature ranging from 50 to 170° C.; preferably, the heating of the mold is performed at a temperature ranging from 80 to 120° C.

In another embodiment, said mold is heated for a period ranging between 0.5 and 50 minutes; preferably, said mold is heated for a period ranging between 1 minute and 40 minutes; more preferably, said mold is heated for a period ranging between 2 minutes and 30 minutes.

In another embodiment, said heating of the mold is performed at a temperature ranging from 80 to 120° C., for a period ranging between 2 minutes and 30 minutes.

Alternatively, when the polymer matrix core and the polymeric membrane are placed in a mold, and said mold is heated, pressure may be also applied to the mold. In a particular embodiment of the present application, the step of providing the resulting polymer matrix core with a polymeric coating is performed by covering said resulting polymeric matrix core with a polymeric membrane in a mold, and said mold is heated under pressure.

In an embodiment, said heating of the mold under pressure is performed at a temperature ranging from 50 to 150° C.; preferably, the heating of the mold is performed at a temperature ranging from 80 to 120° C.

In another embodiment, said mold is heated under pressure for a period ranging between 0.5 and 50 minutes; preferably, said mold is heated under pressure for a period ranging between 1 minute and 40 minutes; more preferably, said mold is heated under pressure for a period ranging between 2 minutes and 30 minutes.

In another embodiment said mold is heated under pressure at a pressure ranging from 2.5 to 10 N; preferably, said mold is heated under pressure at a pressure ranging from 3.5 to 9 N; more preferably, said mold is heated under pressure at a pressure ranging from 5 to 7.5 N.

In another embodiment, said heating of the mold under pressure is performed at a temperature ranging from 80 to 120° C., for a period ranging between 2 minutes and 30 minutes and at a pressure ranging from 5 to 7.5 N.

In another particular embodiment of the present application, the step of providing the resulting polymeric matrix core with a polymeric coating is performed by extruding said resulting polymeric matrix core with a polymeric membrane.

Extrusion methods use temperatures of about 25° C. to about 180° C. more preferably about 50° C. to about 170° C. The sustained release intraocular drug delivery device may be produced by bringing the temperature to about 60° C. to about 150° C. mixing, such as about 130° C., for a time period of about 0 to 1 hour, 0 to 30 minutes, or 5-15 minutes. For example, a time period may be about 10 minutes, preferably about 0 to 5 min. The sustained release intraocular drug delivery device is then extruded at a temperature of about 50° C. to about 170° C., such as about 75° C.

In other embodiments, the polymeric matrix core may be coated with more than one polymer coatings. Said more than one polymer coatings may be applied using different techniques. For example, the first polymer coating may be applied by covering the polymeric matrix core with a polymeric membrane in a mold, and heating said mold, and the second coating may be applied by extruding the resulting polymer matrix core-polymer coating composite with a polymeric membrane.

These processes may be usefully applied to manufacture sustained release intraocular drug delivery devices having a wide array of drug formulations that can be selected to control the release rate profile and various other properties of the therapeutic agent or agents present in the polymeric matrix core.

Another advantage of this manufacture process is that product uniformity can be achieved with ease, without compromising the quality of the product.

The following examples are provided for the purpose of illustrating the present application and by no means should be interpreted to limit the scope of the present invention.

EXAMPLES

Example 1. Manufacture of a Timolol-PDMS Sustained Release Intraocular Drug Delivery Device Timolol (Midas Pharmaceuticals) was ground in a mortar and mixed with PDMS MED-6381 (NuSil Silicone Technology), using a spatula until the mixture was homogeneous (after 2 minutes). The resulting mixture, which contained a concentration of timolol of 50% w/w, was then placed under vacuum for 5 minutes, to remove air bubbles. This mixture was placed into a mold (see FIG. 2) and heated at 80° C. for 30 minutes, to obtain the polymeric matrix core.

Figure 3:
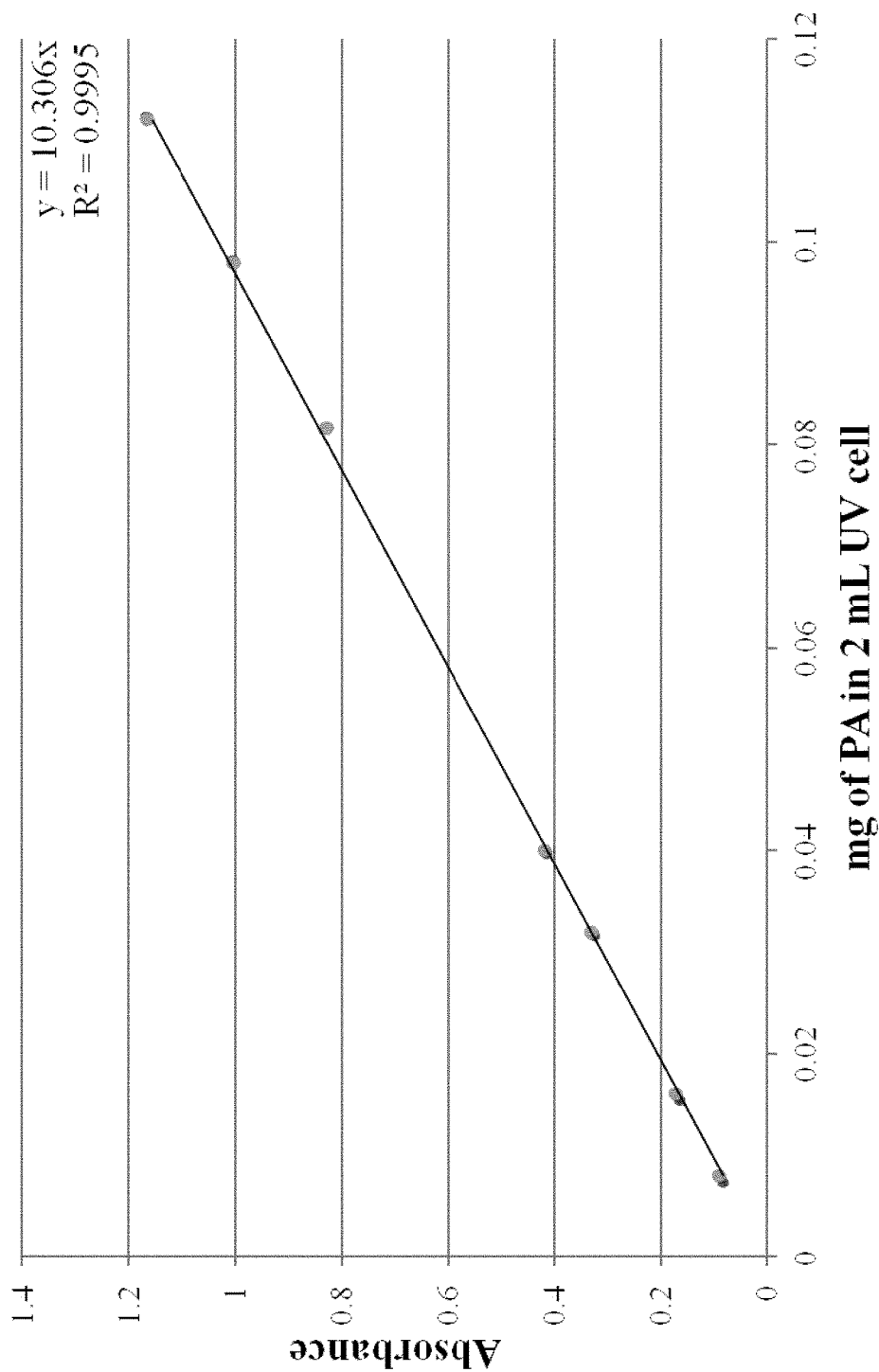
FIG. 3 shows a calibration curve of timolol.

The resulting timolol-containing polymeric matrix core was then pressed between to EVA Elvax 3129 (DuPont®) sheets in a second mold (see FIG. 3). The EVA sheets had a thickness of 100 µm, and were prepared by heating to a temperature of 120° C., under a pressure of 5 N. The mold was then heated for 5 minutes at a temperature of 120° C., applying a pressure of 5 N, to obtain a timolol sustained release intraocular drug delivery device.

Example 2. Manufacture of a Timolol-EVA Sustained Release Intraocular Drug Delivery Device Timolol (Midas Pharmaceuticals) was ground in a mortar and mixed with EVA Elvax 3129 (DuPont®), using a spatula until the mixture was homogeneous (after 2 minutes). The resulting mixture, which contained a concentration of timolol of 50% w/w, was then co-extruded at 120° C. Sheets of the resulting mixture were then obtained by heating the mixture at a temperature of 120° C., under a pressure of 5 N, using a Fontune GTR208 heating press. The resulting sheets had a thickness of at least 130 µm. A polymeric sheet was thus placed in a mold (see FIG. 2) and heated at 120° C. for 5 minutes, applying a pressure of 5 N, to obtain the polymeric matrix core.

The resulting timolol-containing polymeric matrix core was then pressed between to EVA Elvax 3129 (DuPont®) sheets in a second mold (see FIG. 3). The mold was then heated for 5 minutes at a temperature of 120° C., applying a pressure of 5 N, to obtain a timolol sustained release intraocular drug delivery device.

Example 3. In Vitro Release of the Therapeutic Agent

Figure 4:
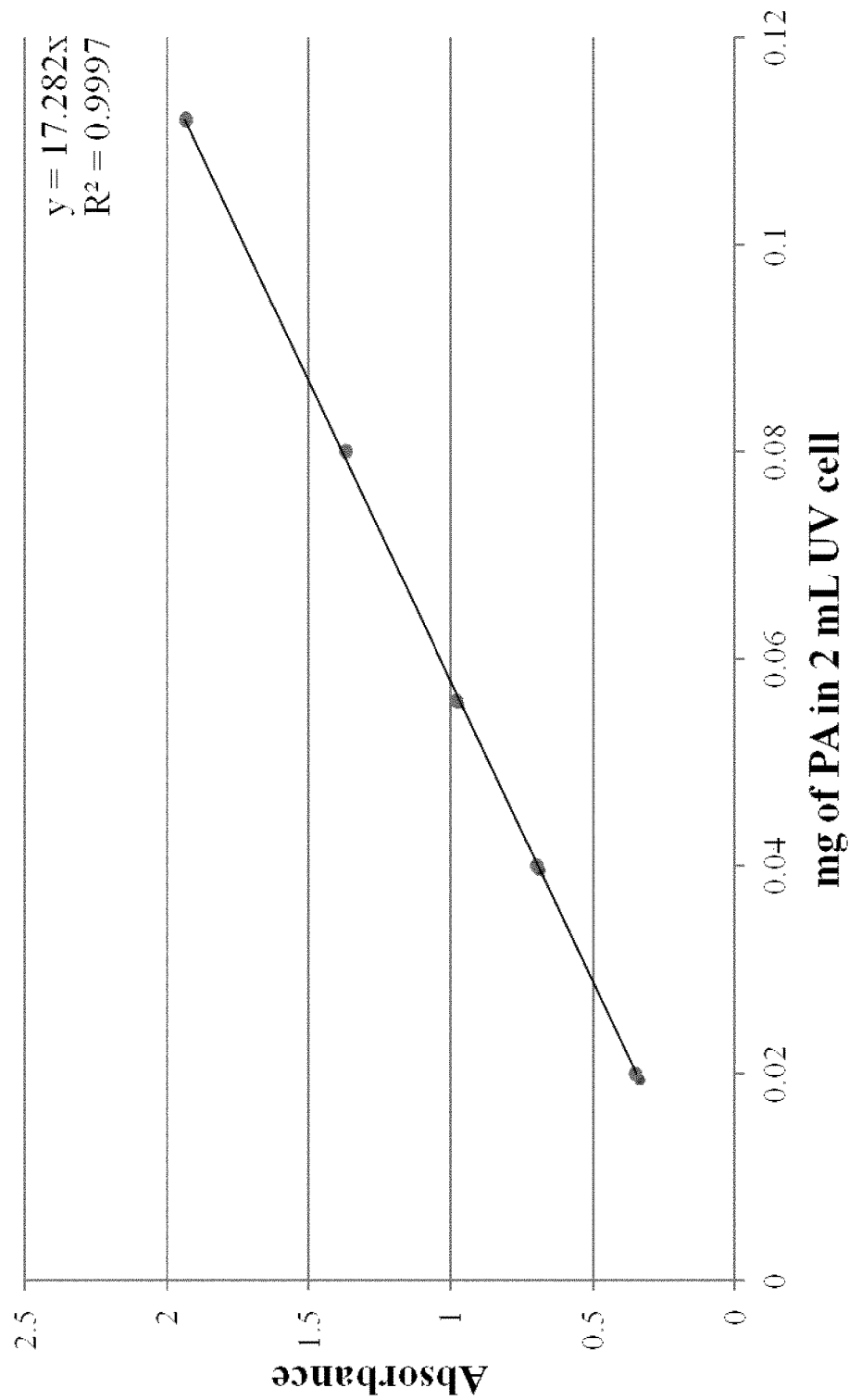
FIG. 4 shows a calibration curve of dorzolamide.
Figure 5:
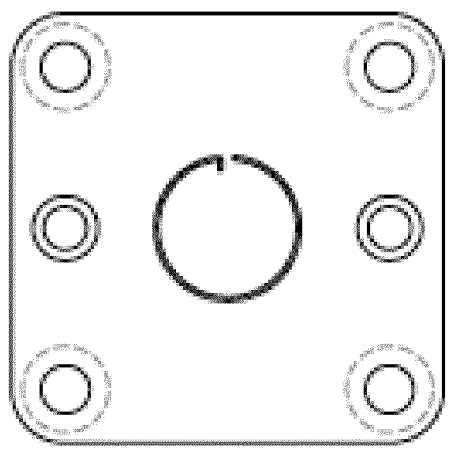
FIG. 5 shows a schematic representation of the mold used to form the polymeric matrix core of the intraocular sustained release drug delivery device, according to an embodiment of the present application.
Figure 5:
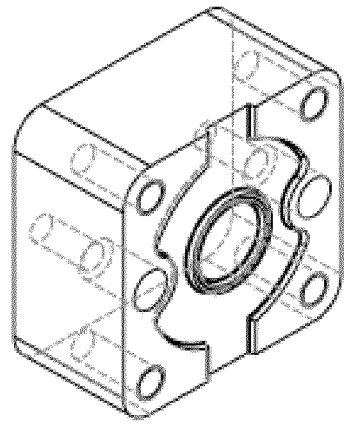
Figure 6:
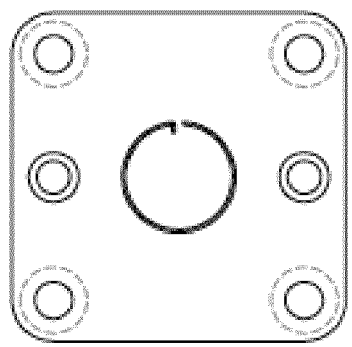
FIG. 6 shows a schematic representation of the mold used to completely surround the polymeric matrix core, with the polymeric coating, to produce the intraocular drug delivery device, according to an embodiment of the present application.
Figure 6:
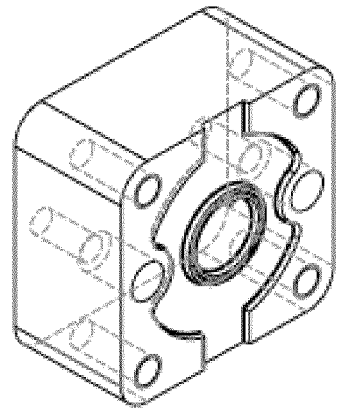

FIGS. 3 and 4 respectively show calibration curves for the determination of the release of timolol and dorzolamide from the intraocular sustained release drug delivery device according to the present application. The calibration curves were determined as follows: a precise quantity of therapeutic agent (timolol or dorzolamide) was dissolved in a precise volume of distilled water. The mixture was stirred with magnetic stirrer until complete dissolution/homogeneity. An aliquot of the mixture (whereof the exact volume is known) was then placed in a UV analysis quartz cell and the absorbance of the sample recorded, using a Hitachi U-330 spectrophotometer, at the UV peak of each therapeutic agent (290 nm for timolol and 250 nm for dorzolamide). Several dilutions of the initial mixture of each therapeutic agent were then prepared, and their individual absorbance readings recorded. The calibration curve was then established, by plotting the absorbance as a function of the concentration of therapeutic agent present in solution.

The device obtained in Example 1 was placed in a container, and 10 ml of distilled water were added. After 5 weeks at room temperature, a sample of 0.1 ml of water was taken from the container and the release of the therapeutic agent was measured by UV spectroscopy (at a λ of 290 nm) and then interpolated with the corresponding calibration curve (FIG. 3), to determine that 7.8 mg of timolol were effectively released from the implant.

Example 4. Mechanical Properties of the Implants

Implants were prepared by molding as described in Example 1 or 2 depending on the type of polymer used, or by laser cutting as indicated in Table 1. Different types of polymer were used for manufacturing the implants as indicated in Table 1, in particular EVA (Elvax 3165 (18% vinyl acetate) or Elvax 3129 (10% vinyl acetate)), HDPE (Lupolen), and PMMA (Diakon).

The mechanical properties of the obtained implants were assessed through a tensile test using an electromechanical tensile tester (Instron 5566, Elancourt, France). All samples were mounted between holders (Pneumatic Action grips, Elancourt, France). Tensile testing was conducted at a rate of 5 mm/min at room temperature (21° C.). Young's modulus (in MPa) and strain at break (%) were automatically calculated by the Instron software (Bluehill 2, Elancourt, France). To obtain Young's modulus, the software calculates the slope of each stress-strain curve in its elastic deformation region (the elastic deformation region of each curve was manually delimitated by moving cursors).

Values of about 390 MPa for Young's modulus, about 15 MPa for stress at break/flow and about 10% for elongation at break are considered to provide suitable rigidity for implantation in the ophthalmological field. The tensil curve of a medical device with these values is shown in FIG. 8.

Figure 8:
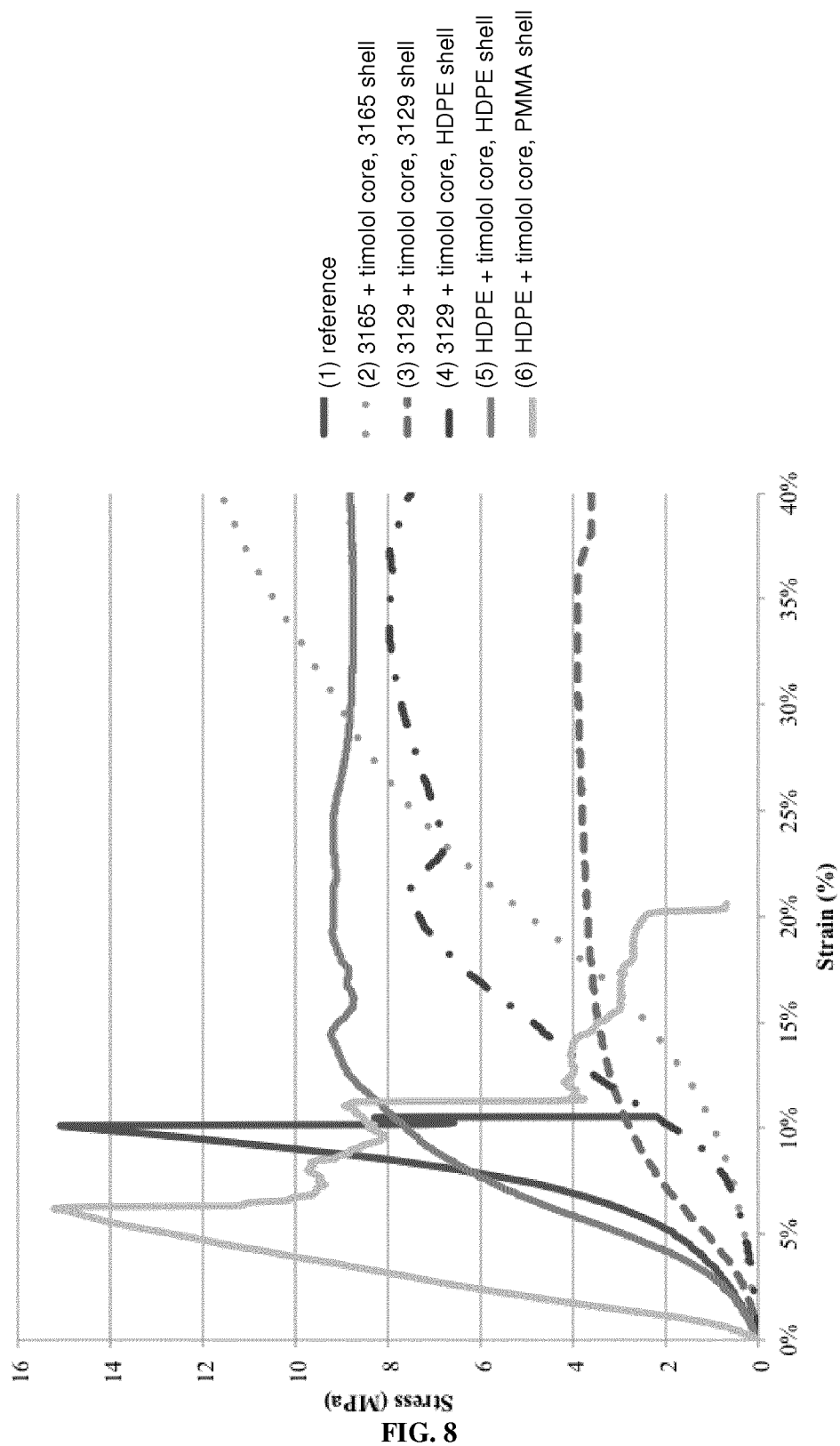
FIG. 8 shows the tensil curves of implants according to embodiments of the present invention prepared by molding and composed of (2) an EVA (18% vinyl acetate)+timolol core and EVA (18% vinyl acetate) shell; (3) an EVA (10% vinyl acetate)+timolol core and EVA (10% vinyl acetate) shell; (4) an EVA (10% vinyl acetate)+timolol core and HDPE shell; (5) a HDPE+timolol core and HDPE shell; and (6) a HDPE+timolol core and PMMA shell. The tensil curve of a reference medical device with values which ensure suitable rigidity for ophthalmological implantation is also shown (1).
Figure 9:
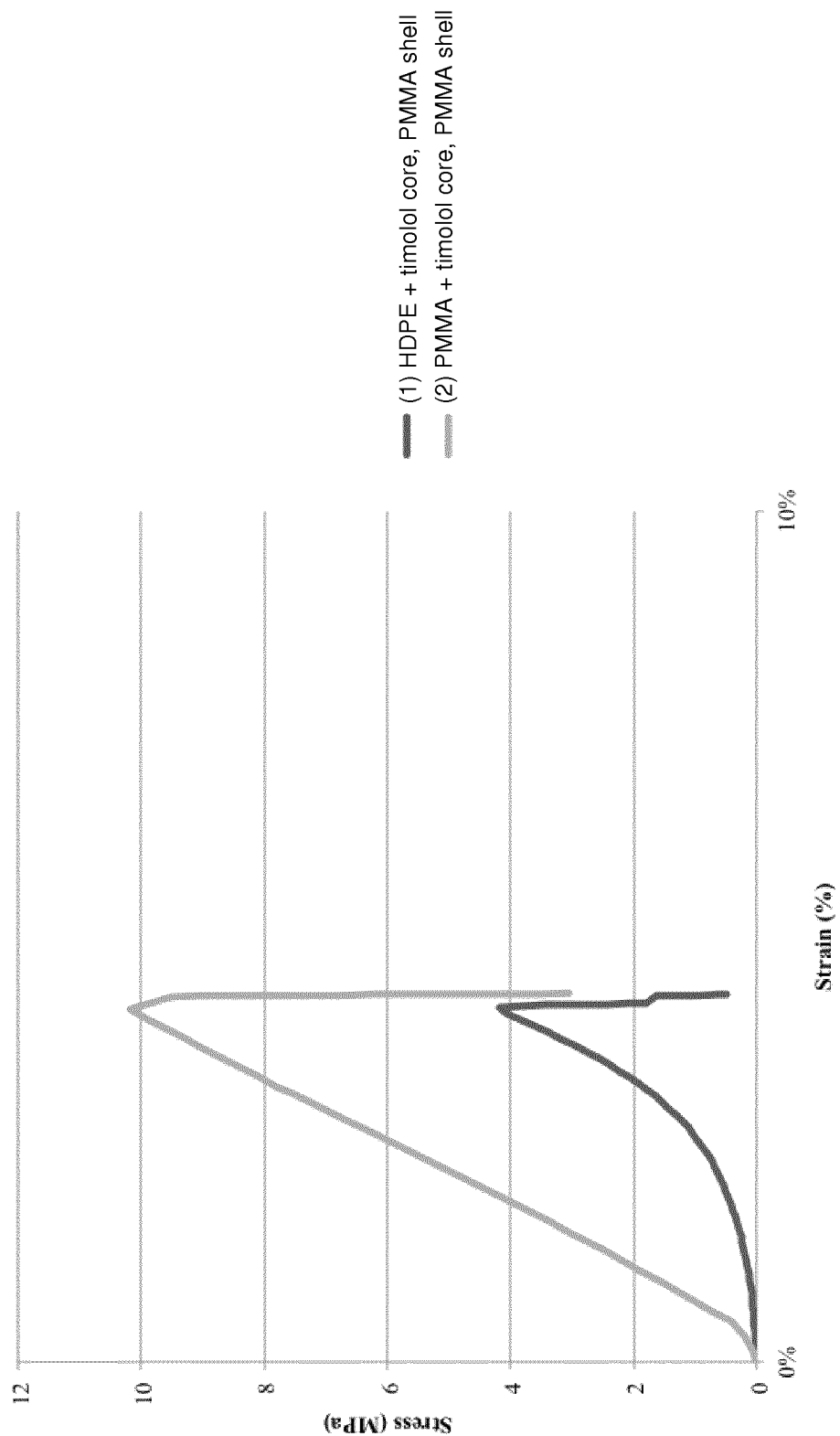
FIG. 9 shows the tensil curves of implants according to embodiments of the present invention prepared by laser cutting and composed of (1) a HDPE+timolol core and PMMA shell; (2) a PMMA+timolol core and PMMA shell.

The tensile curves of the implants are shown in FIGS. 8 and 9, and Young's modulus, stress at break/flow, and elongation at break are summarized in Table 1.

TABLE 1

Young's modulus, stress at break/flow, and elongation at break of implants according to the invention.

| Implant | | | Young's modulus (MPa) | Stress at break/flow (MPa) | Elongation at break (%) |
|---|---|---|---|---|---|
| core | shell | | | | |
| EVA (18% vinyl acetate) + timolol (50/50) | EVA (18% vinyl acetate) | molding | 38 | 27 | ND |
| EVA (10% vinyl acetate) + timolol (50/50) | EVA (10% vinyl acetate) | molding | 40 | 4 | ND |
| EVA (10% vinyl acetate) + timolol (50/50) | HDPE | molding | 70 | 7 | ND |
| HDPE + timolol (50/50) | HDPE | molding | 130 | 9 | ND |
| HDPE + timolol (50/50) | PMMA | molding | 320 | 15 | ND |
| HDPE + timolol (50/50) | PMMA | laser cutting | 240 ± 190 | ND | 5 ± 4 |
| PMMA + timolol (50/50) | PMMA | laser cutting | 268 ± 100 | ND | 5 ± 1 |

ND: not determined.

Implants composed of HDPE and PMMA were considered stiff enough to allow implantation. As shown in FIGS. 8 and 9 and Table 1, such implants have a Young's modulus of at least 240 MPA and a stress at break of at least 15 MPA.

Example 5. Assessment of API Release

Implants were prepared by molding as described in Example 2. The core comprised 50% by weight of timolol and 50% by weight of either EVA (Elvax 3129 (10% vinyl acetate)), HDPE (Lupolen) or PMMA (Diakon). The shell of the implants was composed of EVA (Elvax 3129 (10% vinyl acetate)), HDPE (Lupolen), or PP. Implants without shell were also prepared.

The implants were placed in 10 ml distilled water. At the indicated time points, the medium was renewed, and the release of timolol in the medium was measured by UV spectroscopy (at a λ of 290 nm) and then interpolated with the timolol calibration curve (FIG. 3).

Figure 11:
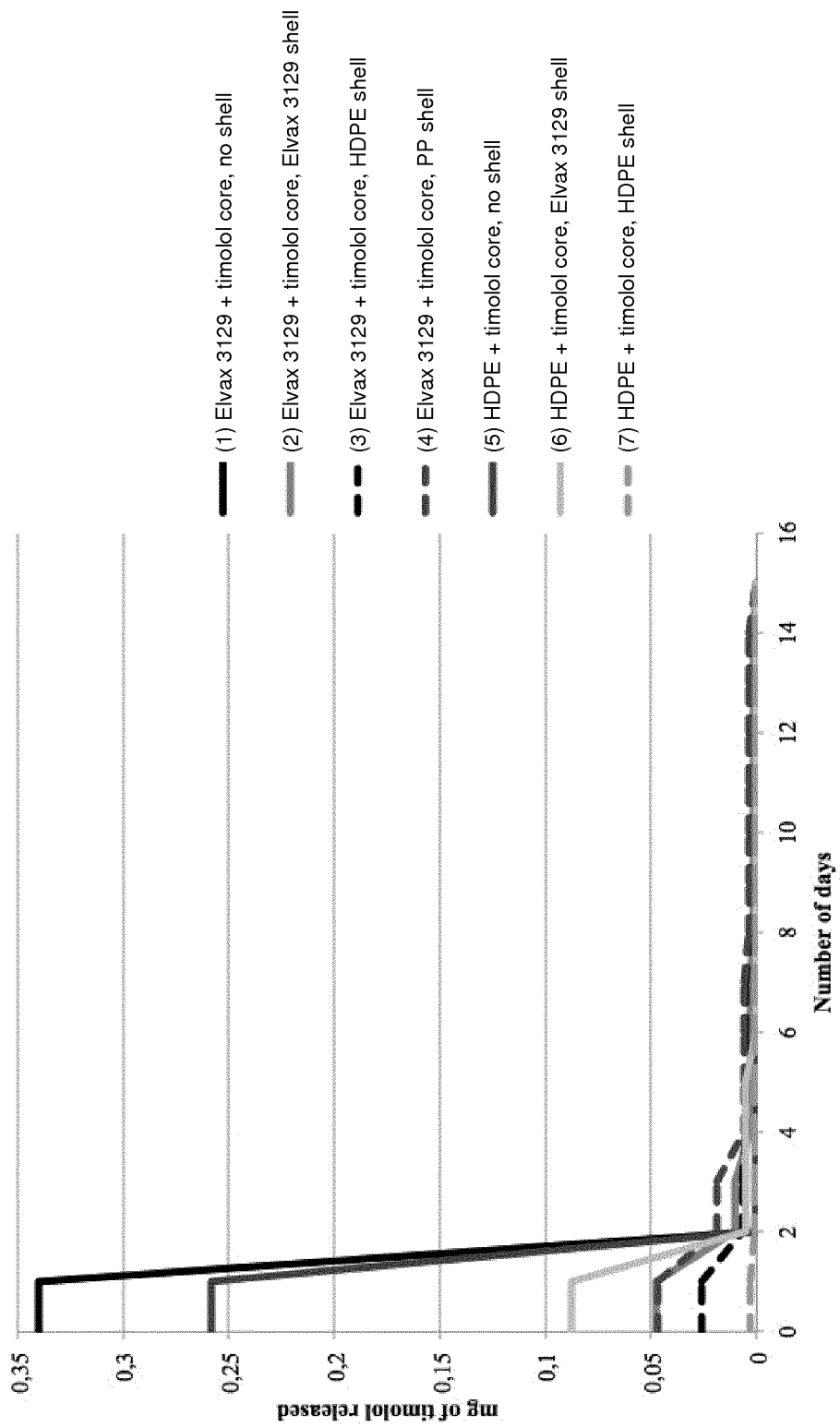
FIG. 11 shows the amount of timolol released from day 0 to day 15 by implants according to embodiments of the present invention composed of (1) an EVA+timolol core and no shell; (2) an EVA+timolol core and EVA shell; (3) an EVA+timolol core and HDPE shell; (4) an EVA+timolol core and PP shell; (5) a HDPE+timolol core and no shell; (6) a HDPE+timolol core and EVA shell; (7) a HDPE+timolol core and HDPE shell.
Figure 12:
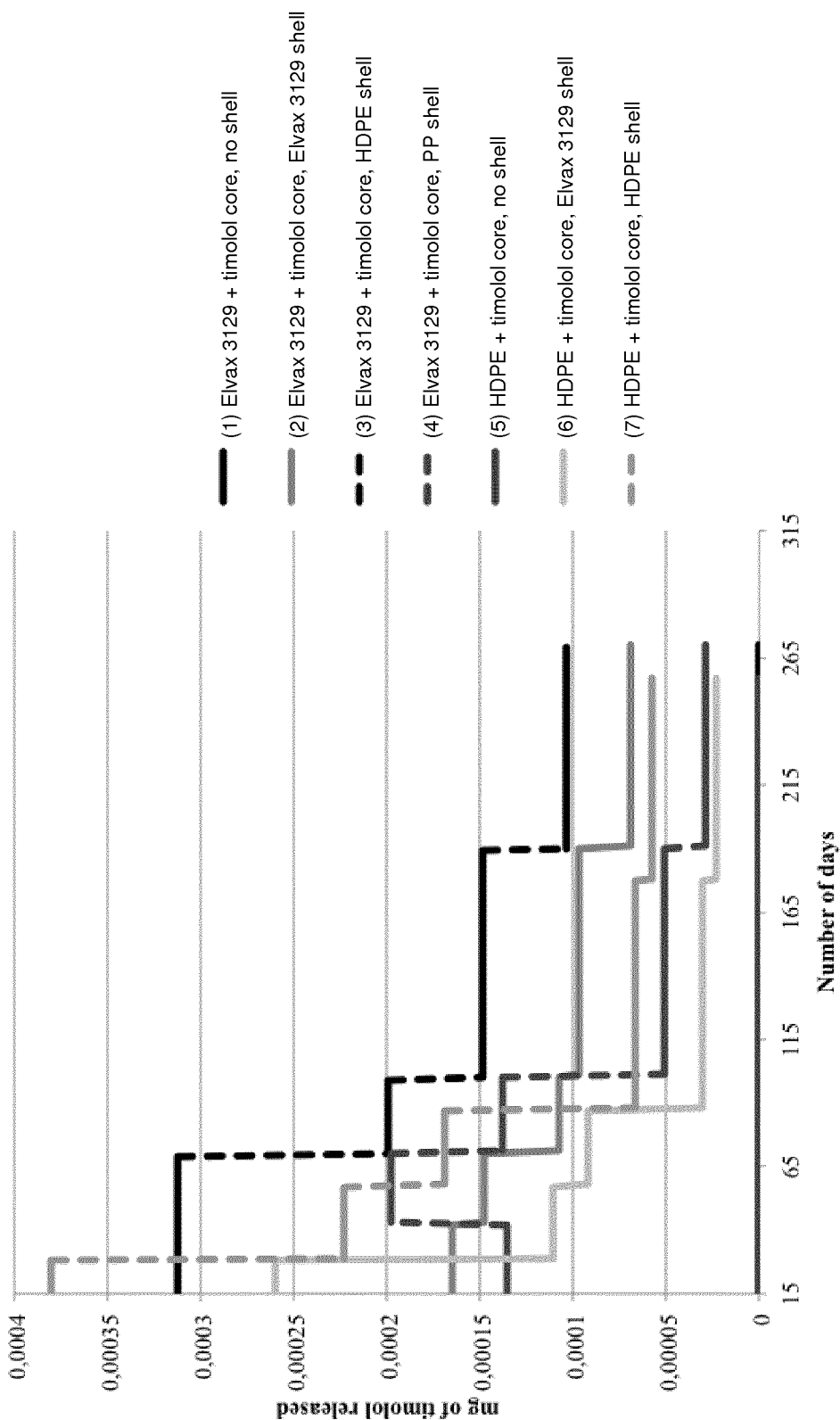
FIG. 12 shows the amount of timolol released from day 15 to day 257 or day 270 by the implants of FIG. 11.
Figure 13:
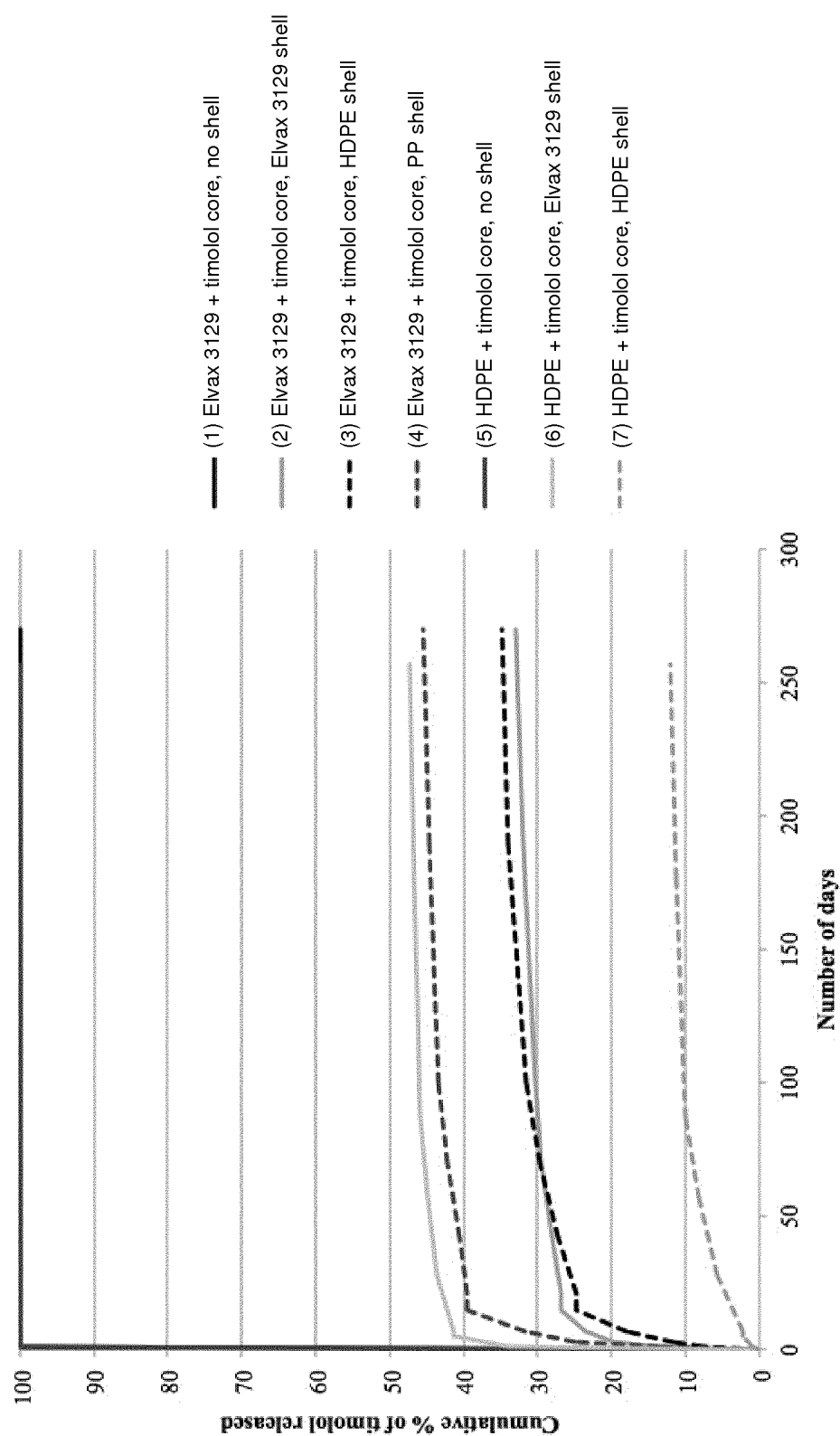
FIG. 13 shows the cumulative percentage of timolol released by the implants of FIG. 11.

FIGS. 11 and 12, and tables 2 and 3 show the amount of timolol released over time. The cumulative percentage of timolol released is shown in FIG. 13.

TABLE 2

Amount (in mg) of timolol released from the implants during the indicated time intervals.

| implant | | D0 to D1 | D1 to D7 | D7 to D100 | D100 to D190 | D190 to D270 | Total release in 270 days |
|---|---|---|---|---|---|---|---|
| core | shell | | | | | | |
| EVA + timolol | — | 0.340 | — | — | — | — | n.a. |

TABLE 2-continued

Amount (in mg) of timolol released from the implants during the indicated time intervals.

| implant | | D0 to D1 | D1 to D7 | D7 to D100 | D100 to D190 | D190 to D270 | Total release in 270 days |
|---|---|---|---|---|---|---|---|
| core | shell | | | | | | |
| EVA + timolol | EVA | 0.047 | 0.033 | 0.023 | 0.009 | 0.006 | 0.118 |
| EVA + timolol | HDPE | 0.026 | 0.035 | 0.046 | 0.013 | 0.008 | 0.128 |
| EVA + timolol | PP | 0.047 | 0.062 | 0.038 | 0.005 | 0.002 | 0.154 | n.a. not applicable

TABLE 3

Amount (in mg) of timolol released from the implants during the indicated time intervals.

| implant | | D0 to D1 | D1 to D7 | D7 to D87 | D87 to D177 | D177 to D257 | Total release in 257 days |
|---|---|---|---|---|---|---|---|
| core | shell | | | | | | |
| HDPE + timolol | — | 0.258 | — | — | — | — | n.a. |
| HDPE + timolol | EVA | 0.088 | 0.019 | 0.012 | 0.003 | 0.002 | 0.124 |
| HDPE + timolol | HDPE | 0.003 | 0.003 | 0.020 | 0.006 | 0.005 | 0.037 |
| HDPE + timolol | — | 0.190 | — | — | — | — | n.a. |
| PMMA + timolol | — | 0.242 | — | — | — | — | n.a. |

The present example shows that timolol can be released from an EVA, a HDPE, and a PMMA core. Implants without shell released all their timolol in one day, whereas implants with shell still release timolol after 9 or 8.5 months.

The invention claimed is:

1. A sustained release intraocular drug delivery device having the shape of a compliant annular segment configured for a sulcus of a human eye, comprising:
    (a) an annular rod shaped solid polymeric matrix core into which at least one therapeutic agent is mixed, and;
    (b) a solid polymeric coating completely surrounding said polymeric matrix material;
    wherein said polymeric matrix core and polymeric coating are insoluble and inert in ocular fluids, and wherein said sustained release intraocular drug delivery device has a cross sectional diameter ranging from 0.10 to 0.80 mm,
    wherein the annular segment ranges from 90 to 360 degrees of the ring; and
    wherein the polymeric coating regulates the release of the therapeutic agent contained in the polymeric matrix material.

2. The device according to claim 1, wherein said polymeric matrix core has a cross-sectional diameter of 0.1 mm to 0.48 mm.

3. The device according to claim 1, wherein said polymeric coating is a polymeric membrane with a thickness ranging from 0.05 to 0.32 mm.

4. The device according to claim 1, wherein said annular segment has length configured to extend along from 180 to 360° of the sulcus.

5. The device according to claim 1, wherein said polymeric matrix core comprises a polymer selected from the group consisting of ethylene-co-vinylacetate, poly(dimethylsiloxane), polypropylene, high density polyethylene, plasticized polyethylene terephthalate, poly(methyl methacrylate), polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4-isopropylidene diphenylene carbonate), vinylidene chloride, acrylonitrile copolymer, vinyl chloride-diethyl fumerale copolymer, silicone rubbers, ethylene-propylene rubber, silicone-carbonate copolymers, vinylidene chloride-vinyl chloride copolymer, vinyl chloride-acrylonitrile copolymer and vinylidene chloride-acrylonitrile copolymer, polycarbonate, polyurethane, thermoplastic elastomers (TPE), SEBS (styrene-ethylene-butylene-styrene), SBS (styrene-butadiene-styrene), MBM (methylmethacrylate-butadiene-methylmethacrylate)), and combinations thereof.

6. The device according to claim 5, wherein said polymeric matrix core comprises a polymer selected from the group consisting of high density polyethylene, poly(methyl methacrylate), and combinations thereof.

7. The device according to claim 5, wherein said polymeric matrix core comprises from 1.0 to 50% by weight of said at least one therapeutic agent.

8. The device according to claim 5, wherein said polymeric coating comprises a polymer selected from the group consisting of ethylene-co-vinylacetate, poly(dimethylsiloxane), polypropylene, polyethylene, plasticized polyethylene terephthalate, poly(methyl methacrylate), crosslinked polyvinyl alcohol, polyolefins or polyvinyl chlorides or cross-linked gelatins; regenerated, insoluble, nonerodible cellulose, acylated cellulose, esterified celluloses, cellulose acetate propionate, cellulose acetate butyrate, cellulose acetate phthalate, cellulose acetate diethyl-aminoacetate; polyurethanes, polycarbonates, and microporous polymers formed by co-precipitation of a polycation and a polyanion modified insoluble collagen, and combinations thereof.

9. The device according to claim 8, wherein said polymeric coating comprises a polymer selected from the group consisting of polyethylene, high density polyethylene, poly(methyl methacrylate), and combinations thereof.

10. The device according to claim 1,
    wherein said polymeric matrix core comprises a polymer selected from the group consisting of high density polyethylene, poly(methyl methacrylate), and combinations thereof;
    wherein said polymeric coating comprises a polymer selected from the group consisting of high density polyethylene, poly(methyl methacrylate), and combinations thereof;
    wherein said at least one therapeutic agent is selected from the group consisting of antibiotic agents, antibacterial agents, antiviral agents, prostaglandin analogues, anti-glaucoma agents, antiallergenic agents, anti-inflammatory agents, anti-angiogenesis agents, immune system modifying agents, anti-cancer agents, antisense agents, antifungal agents, myotic and anticholinesterase agents, mydriatic agents, differentiation modulator agents, sympathomimetic agents, anaesthetic agents, vasoconstrictive agents, vasodillatory agents, decongestants, cell transport/mobility impending agents, polypeptides and protein agents, steroidal agents, carbonic anhydrase inhibitor agents, polycations, polyanions, and lubricating agents.

11. The device according to claim 10, wherein said at least one therapeutic agent is selected from the group consisting of prostaglandin analogues, anti-glaucoma agents, anti-inflammatory agents, anti-angiogenesis compounds, and immune system modifying agents.

12. The device according to claim 10, wherein said at least one therapeutic agent is selected from the group consisting of bevacizumab, ranibizumab, aflibercept, timolol, latanoprost, dorzolamide, triamcinolone, dexamethasone, and cyclosporin.

13. The device according to claim 4, wherein said polymeric matrix core comprises polyethylene, and wherein said polymeric coating comprises polyethylene, high density polyethylene, or poly(methyl methacrylate).

14. The device according to claim 4, wherein said polymeric matrix core comprises poly(methyl methacrylate), and wherein said polymeric coating comprises polyethylene, high density polyethylene, or poly(methyl methacrylate).

15. The device according to claim 13, wherein said at least one therapeutic agent comprises timolol.

16. A method of treatment of ocular diseases comprising administering a therapeutic agent incorporated within a sustained release intraocular drug delivery device according to claim 1, and wherein said sustained release intraocular drug delivery device is inserted into the sulcus of the human eye.

17. The method of treatment according to claim 16, wherein the therapeutic agent is selected from the group consisting of: bevacizumab, ranibizumab, aflibercept, timolol, latanoprost, dorzolamide, triamcinolone, dexamethasone, and cyclosporine.

18. The method according to claim 17, wherein said therapeutic agent is selected from the group consisting of: timolol, triamcinolone, dexamethasone, and cyclosporine.

19. A process for preparing a sustained release intraocular drug delivery device, comprising:
mixing the at least one therapeutic agent with an insoluble and inert polymer;
molding and/or extruding said mixture to form a solid polymeric matrix core; and,
providing the resulting polymeric matrix core with a polymeric coating, wherein the polymeric coating is a solid and completely surrounding said polymeric matrix material;
wherein said polymeric matrix core and polymeric coating are insoluble and inert in ocular fluids, and
wherein said sustained release intraocular drug delivery device forms a compliant annular segment having a cross sectional diameter ranging from 0.10 to 0.80 mm and length sufficient to extend along 90 to 360 degrees of the sulcus of the human eye.

20. The process of claim 19, wherein the step of providing the resulting polymer matrix core with a polymeric coating is performed by covering said resulting polymeric matrix core with a polymeric membrane in a mold, and heating said mold.

21. The process according to claim 20, for use in manufacturing an intraocular device for the treatment of ocular diseases by inserting said device in the sulcus of the eye.

22. A surgical method for inserting or implanting the device according to claim 1, comprising the steps of partially straightening the device by applying force, inserting the device in the sulcus of the human eye, and releasing said device.

23. The device according to claim 1,
wherein the said polymeric matrix core comprises a polymer selected from the group of ethylene-co-vinylacetate, a polyurethane, a polyolefin, and combinations thereof;
wherein said polymeric coating comprises a polymer selected from the group of ethylene-co-vinylacetate, a polyurethane, a polyolefin, and combinations thereof; and
wherein said at least one therapeutic agent is selected from the group consisting of antibiotic agents, antibacterial agents, antiviral agents, prostaglandin analogues, anti-glaucoma agents, antiallergenic agents, anti-inflammatory agents, anti-angiogenesis agents, immune system modifying agents, anti-cancer agents, antisense agents, antifungal agents, myotic and anticholinesterase agents, mydriatic agents, differentiation modulator agents, sympathomimetic agents, anaesthetic agents, vasoconstrictive agents, vasodillatory agents, decongestants, cell transport/mobility impending agents, polypeptides and protein agents, steroidal agents, carbonic anhydrase inhibitor agents, polycations, polyanions, and lubricating agents.

24. The device according to claim 23, wherein said at least one therapeutic agent is selected from the group consisting of prostaglandin analogues, anti-glaucoma agents, anti-inflammatory agents, anti-angiogenesis compounds, and immune system modifying agents.

25. The device according to claim 23, wherein said at least one therapeutic agent is selected from the group consisting of bevacizumab, ranibizumab, aflibercept, timolol, latanoprost, dorzolamide, triamcinolone, dexamethasone, and cyclosporin.

26. The device according to claim 1, wherein said polymeric matrix core comprises polyethylene, ethylene-co-vinylacetate, a polyurethane, or a polyolefin, and wherein said polymeric coating comprises polyethylene, high density polyethylene, poly(methyl methacrylate), ethylene-co-vinylacetate, a polyurethane, or a polyolefin.

27. The device according to claim 1, wherein said polymeric matrix core comprises poly(methyl methacrylate), ethylene-co-vinylacetate, a polyurethane, or a polyolefin, and wherein said polymeric coating comprises polyethylene, high density polyethylene, poly(methyl methacrylate), ethylene-co-vinylacetate, a polyurethane, or a polyolefin.

28. The device according to claim 26, wherein said at least one therapeutic agent comprises timolol.

29. A method of treatment of ocular diseases comprising administering a therapeutic agent incorporated within a sustained release intraocular drug delivery device according to claim 23, and wherein said sustained release intraocular drug delivery device is inserted into the sulcus of the human eye.

30. The method of treatment according to claim 29, wherein the therapeutic agent is selected from the group consisting of: bevacizumab, ranibizumab, aflibercept, timolol, latanoprost, dorzolamide, triamcinolone, dexamethasone, and cyclosporine.

* * * * *